US012235269B2

(12) United States Patent
Vashist et al.

(10) Patent No.: US 12,235,269 B2
(45) Date of Patent: Feb. 25, 2025

(54) IMMUNOASSAY FOR SARS-COV-2 ANTIBODIES

(71) Applicant: PICTOR LIMITED, Auckland (NZ)

(72) Inventors: Sandeep Kumar Vashist, Aachen (DE); Lionel Gilles Guiffo Djoko, Auckland (NZ); Bhavesh Govind, Auckland (NZ)

(73) Assignee: Pictor Limited, Auckland (NZ)

( * ) Notice: Subject to any disclaimer, the term of this patent is extended or adjusted under 35 U.S.C. 154(b) by 734 days.

(21) Appl. No.: 17/428,967

(22) PCT Filed: Jul. 29, 2021

(86) PCT No.: PCT/NZ2021/050116
§ 371 (c)(1),
(2) Date: Aug. 5, 2021

(87) PCT Pub. No.: WO2022/025773
PCT Pub. Date: Feb. 3, 2022

(65) Prior Publication Data
US 2022/0163528 A1 May 26, 2022

(30) Foreign Application Priority Data

Jul. 29, 2020 (NZ) ........................ 766621

(51) Int. Cl.
*G01N 33/68* (2006.01)
*C12Q 1/70* (2006.01)
(Continued)

(52) U.S. Cl.
CPC . *G01N 33/56983* (2013.01); *G01N 33/54386* (2013.01); *G01N 33/6854* (2013.01);
(Continued)

(58) Field of Classification Search
None
See application file for complete search history.

(56) References Cited

U.S. PATENT DOCUMENTS

| 6,417,324 B1 | 7/2002 | Sallberg |
| 6,699,665 B1 | 3/2004 | Kim et al. |

(Continued)

FOREIGN PATENT DOCUMENTS

| CA | 2509063 | 6/2004 |
| CA | 2606815 | 11/2006 |

(Continued)

OTHER PUBLICATIONS

Ji et al., "Detection of COVID-19: A review of the current literature and future perspectives", Biosensors and Bioelectronics, Jul. 2020, 166:112455, 18 pages.

(Continued)

*Primary Examiner* — Shanon A. Foley
(74) *Attorney, Agent, or Firm* — DLA Piper LLP (US)

(57) ABSTRACT

Severe acute respiratory syndrome coronavirus 2 (SARS-CoV-2) is the strain of coronavirus that causes coronavirus disease 2019 (COVID-19), the respiratory illness responsible for the COVID-19 pandemic. Antibodies produced from an immune response against SARS-CoV-2 are used to analyze prior exposure to the virus. The present invention provides methods for detecting antibodies in response to SARS-CoV-2 infection in a single multiplex immunoassay.

21 Claims, 11 Drawing Sheets

(51) Int. Cl.
  *G01N 33/543*    (2006.01)
  *G01N 33/569*    (2006.01)
(52) U.S. Cl.
  CPC ... *G01N 2333/165* (2013.01); *G01N 2496/15* (2013.01); *G01N 2800/26* (2013.01)

(56) References Cited

U.S. PATENT DOCUMENTS

| | | | |
|---|---|---|---|
| 7,074,194 | B2 | 7/2006 | Crosby et al. |
| 9,625,453 | B2 | 4/2017 | Kumble |
| 10,948,486 | B2 | 3/2021 | Kumble |
| 11,703,507 | B2 * | 7/2023 | Vashist ............ G01N 33/54386 435/5 |
| 2003/0026739 | A1 | 2/2003 | MacBeath et al. |
| 2003/0109420 | A1 | 6/2003 | Valkirs et al. |
| 2003/0153013 | A1 | 8/2003 | Huang |
| 2004/0191810 | A1 | 9/2004 | Yamamoto |
| 2005/0003398 | A1 | 1/2005 | Tao et al. |
| 2005/0153381 | A1 | 7/2005 | Marusich et al. |
| 2005/0211559 | A1 | 9/2005 | Kayyem |
| 2006/0024703 | A1 | 2/2006 | Zhang et al. |
| 2007/0225206 | A1 | 9/2007 | Ling et al. |
| 2009/0118133 | A1 | 5/2009 | Melrose |
| 2020/0261907 | A1 | 8/2020 | Xie et al. |
| 2022/0065807 | A1 | 3/2022 | Gao et al. |

FOREIGN PATENT DOCUMENTS

| | | |
|---|---|---|
| CA | 2664108 | 3/2008 |
| CN | 111024954 A | 4/2020 |
| WO | WO 2000/005579 | 2/2000 |
| WO | WO 2005/093419 | 10/2005 |
| WO | WO 2008067091 A2 | 6/2008 |

OTHER PUBLICATIONS

Sela-Culang et al., "The structural basis of antibody-antigen recognition", Frontiers in Immunology, 2013, 4:302, 13 pages.
Yellapu et al., "Evolutionary Analysis of Severe Acute Respiratory Syndrome Coronavirus 2 (SARS-CoV-2) Reveals Genomic Divergence with Implications for Universal Vaccine Efficacy", Vaccines. Oct. 2020, 8:591, 15 pages.
Amrun, "Linear B-cell epitopes in the spike and nucleocapsid proteins as markers of SARS-CoV-2 exposure and disease severity", EBioMedicine, Jul. 29, 2020, 58:102911-102919.
BioCan, "Tell Me Fast Novel Coronavirus (COVID-19) IgG/IgM Antibody Test", Biocan, Jun. 3, 2020, 8 pages.
Boster Biological Technology [online], "SARS-CoV-2 Human IgG (4-Plex)", [retrieved from internet on Oct. 22, 2021], URL: https://web.archive.org/web/20200528034845/https://www.bosterbio.com/multiplex-covid-19-biomarkers-assay-sars-cov-2-human-igg-4-plex> published on May 28, 2020 as per Wayback Machine.
Liu et al., "Development of a quantum-dot lateral flow immunoassay strip based portable fluorescence smart-phone system for ultrasensitive detection of IgM/IgG to SARS-CoV-2", medRxiv, Jul. 24, 2020, 18 pages.
PCT International Search Report and Written Opinion in International Application No. PCT/NZ2021/050116, dated Nov. 1, 2021, 12 pages.
Rosado et al., "Serological signatures of SARS-CoV-2 infection: Implications for antibody-based diagnostics", medRxiv, Jun. 2020, 39 pages.
Roxhed et al., "A translational multiplex serology approach to profile the prevalence of anti-SARS-CoV-2 antibodies in home-sampled blood", medRxiv, Jul. 2, 2020, 47 pages.
Bates et al., "Cross-reactivity of SARS-CoV structural protein antibodies against SARS-CoV-2", Cell Reports, Feb. 2021, 34:108737, 16 pages.
Longley et al., "Asymptomatic Plasmodium vivax infections induce robust IgG responses to multiple blood-stage proteins in a low-transmission region of western Thailand", Malaria Journal, 2017, 16:178, 13 pages.
Lu et al., "Genomic characterization and epidemiology of 2019 novel coronavirus: implications for virus origins and receptor binding", The Lancet, Feb. 2020, 495: 565-574.
US Non-Final Office Action in U.S. Appl. No. 17/396,263, dated Nov. 10, 2022, 19 pages.
Bangham et al., "Protein microarray-based screening of antibody specificity", Methods Mol. Med., 2005, 144:173-182.
Canadian Office Action regarding application 2,670,615.
Haab, "Methods and application of antibody microarrays in cancer research", Proteomics, 2003, 3:2116-2122.
Huang et al., "Simultaneous detection of multiple cytokines from conditioned media and patient's sera by an antibody-based protein array system", Analytical Biochemistry, 2001, 294: 55-62.
Invitrogen, "ProtoArray® Applications Guide", ThermoFischer Scientific, 2015, 136 pages.
Kastenbauer et al., "Patterns of protein expression in infectious meningitis: a cerebrospinal fluid protein array analysis", J. Neuroimmunol., 164(1-2):134-139 (2005).
Kokubun et al., "Serum Amyloid A (SAA) concentration varies among rheumatoid arthritis patients estimated by SAA/CRP ratio", Clinica Chimica Acta, 360:97-102 (2005).
Li et al., "Protein array method for assessing in vitro biomaterial-induced cytokine expression", Biomaterials, 26(10): 1081-1085 (2005).
Masters et al., "Diagnostics challenges for multiplexed protein micorrays", Drug Discovery Today, Nov. 2006, 11:1007-1011.

* cited by examiner

FIG. 1
Detection of Human IgG
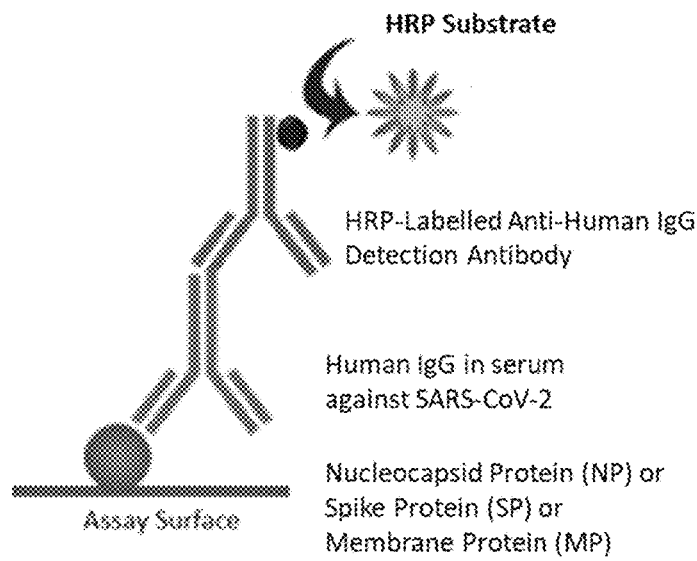
FIGS. 2 A-E
PictArray™ COVID-19 MIA Procedure
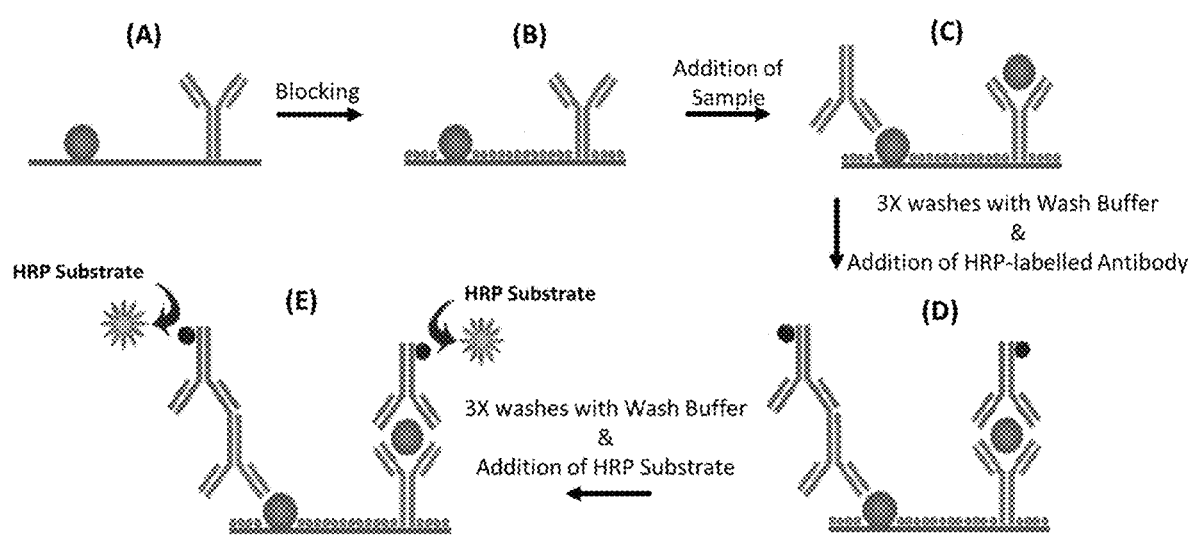

FIGS. 3A-B
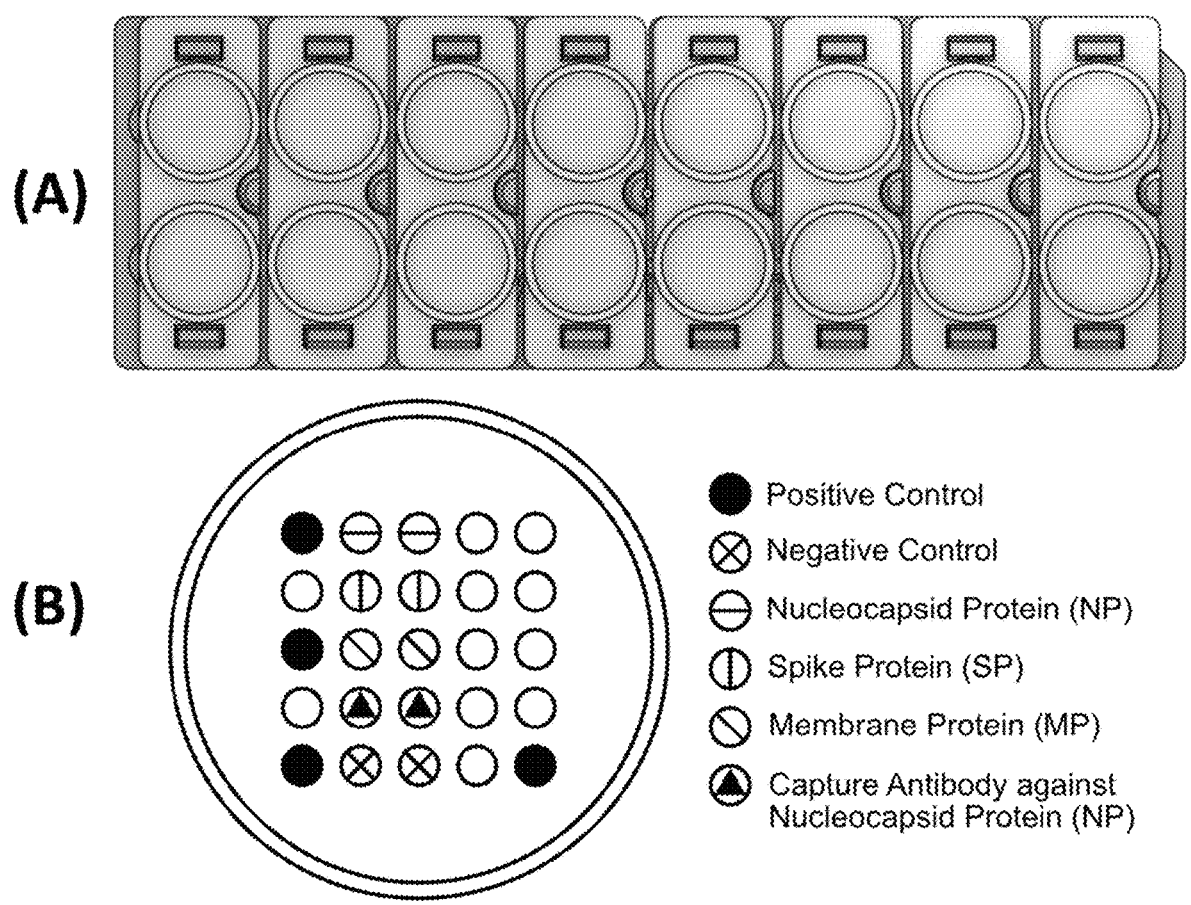

FIGS. 4A-B
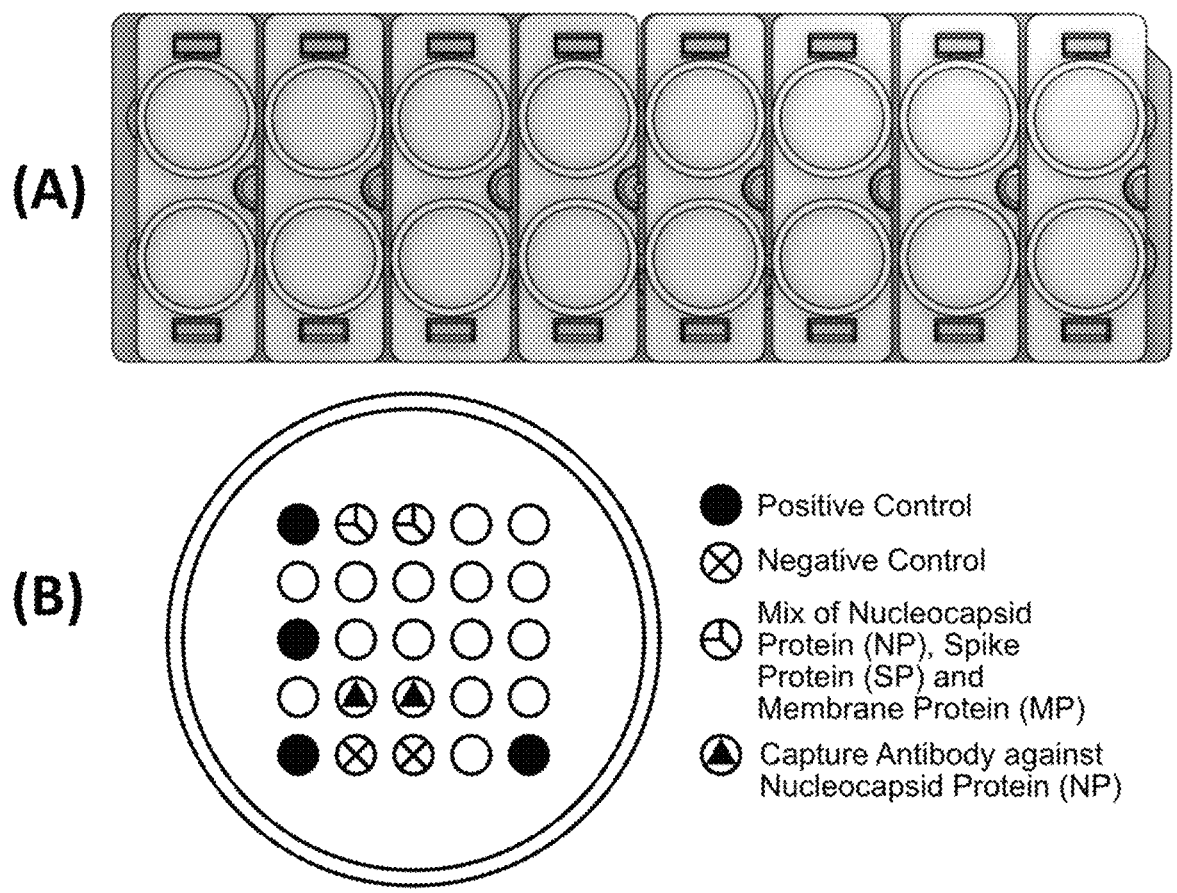

FIGS. 5A-B
(A)
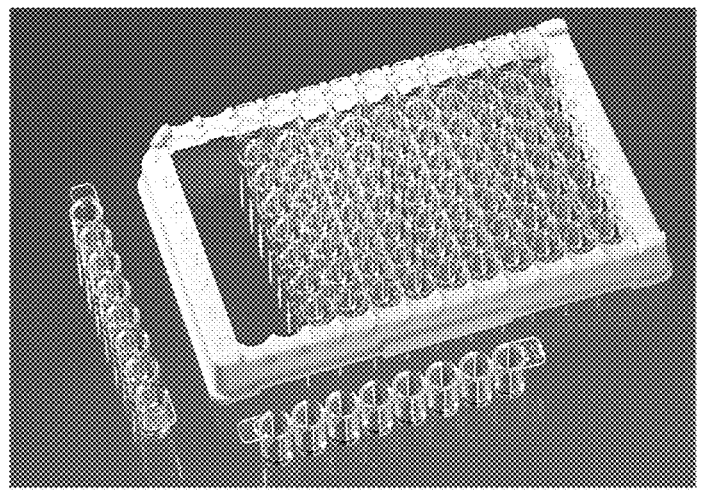
(B)
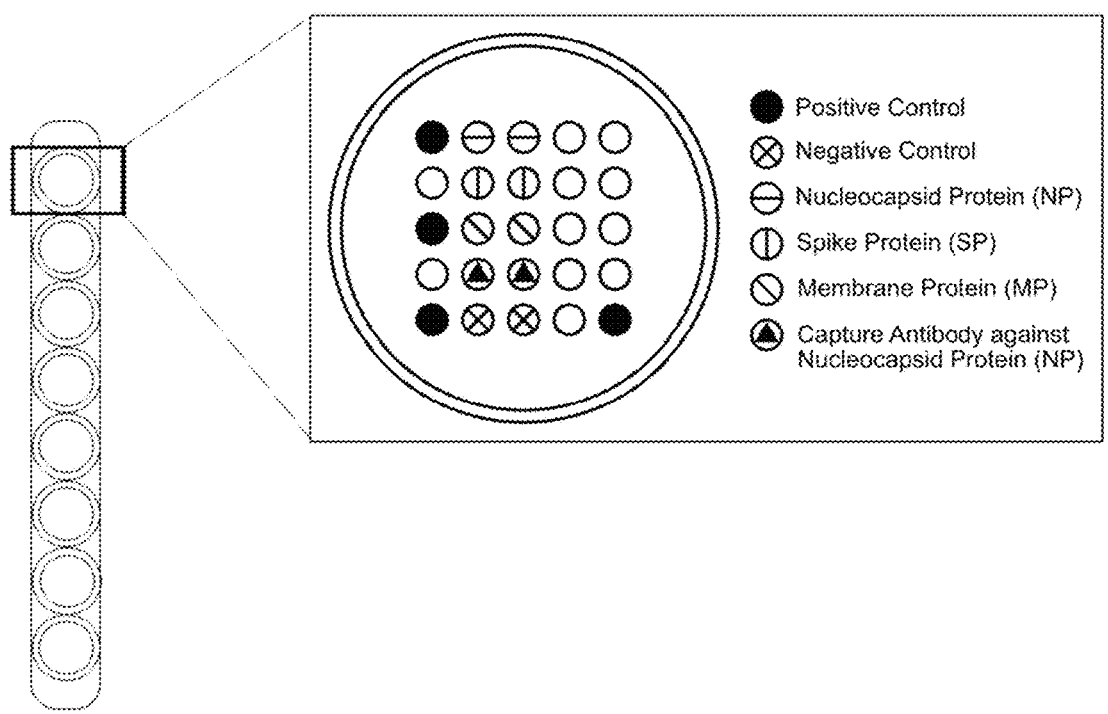

FIGS. 6A-B
(A)
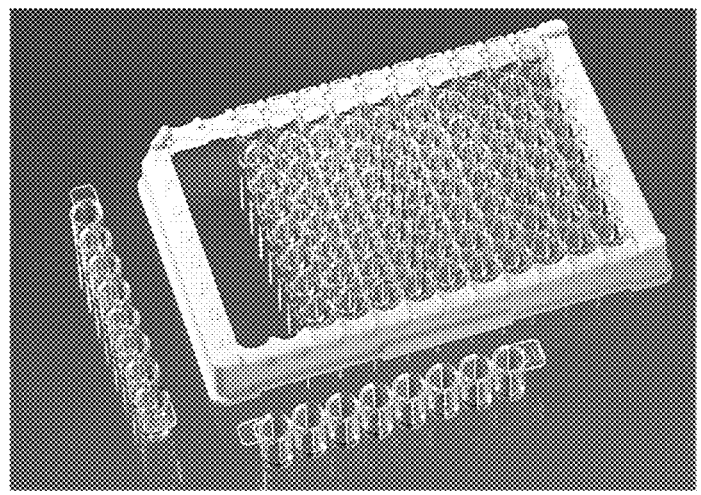
(B)
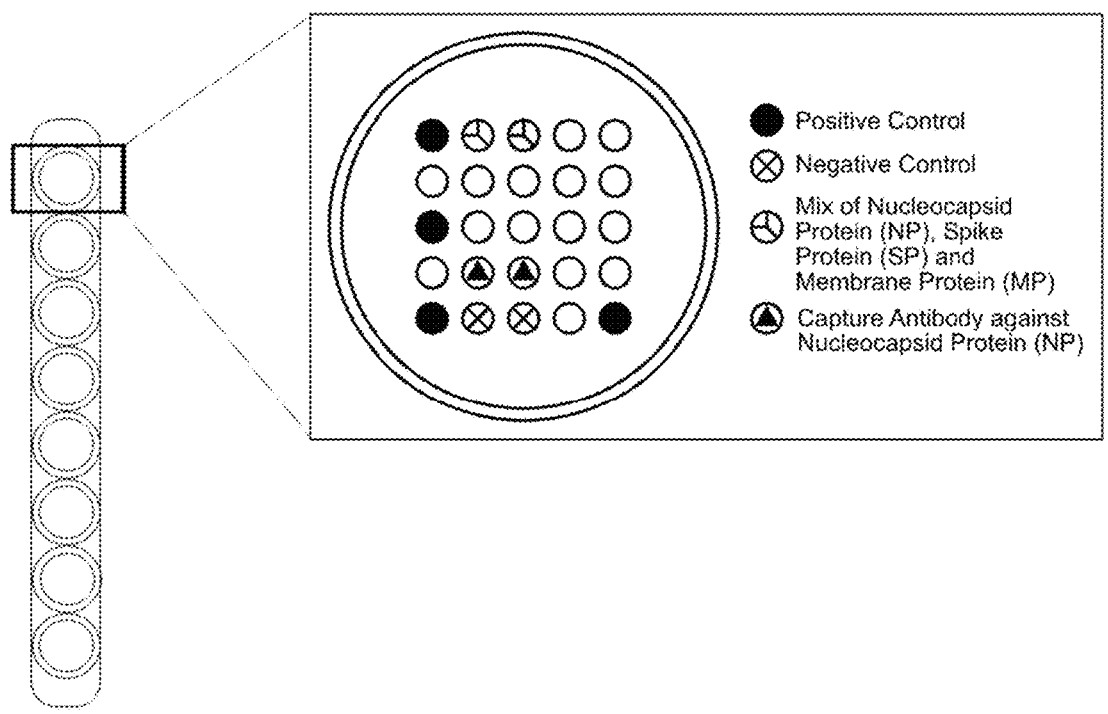

FIGS. 7A-B
(A) 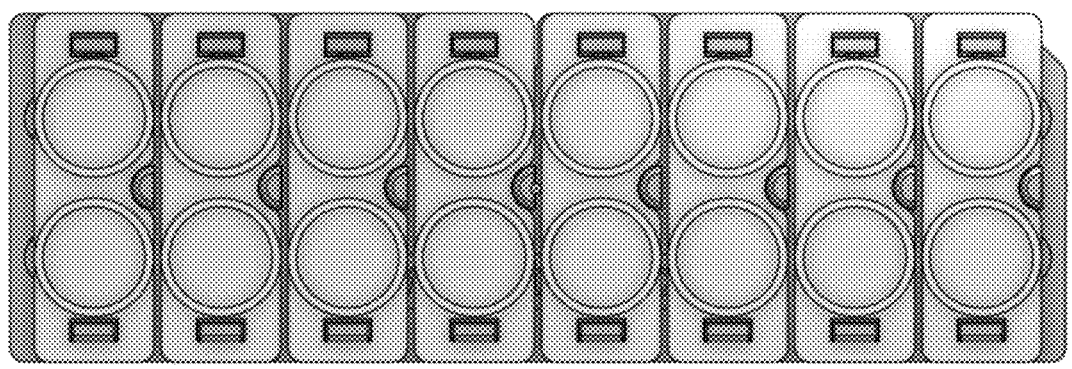
(B) 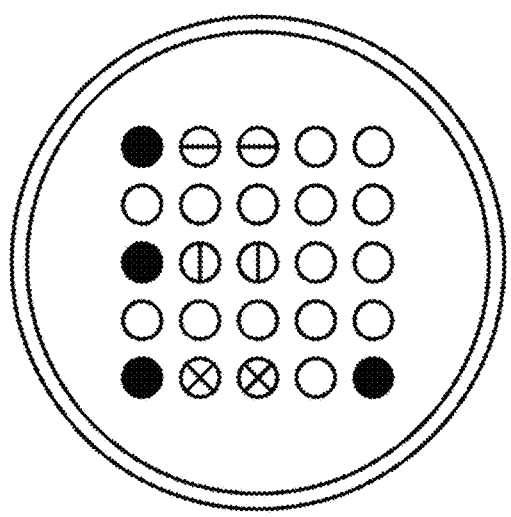
● Positive Control
⊖ Nucleocapsid Protein (NP)
Ⓘ Spike Protein (SP)
⊗ Negative Control FIGS. 9A-B
(A)
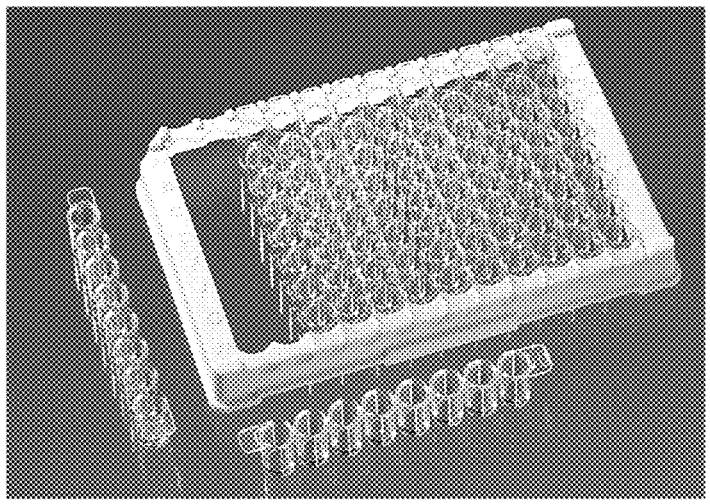
(B)
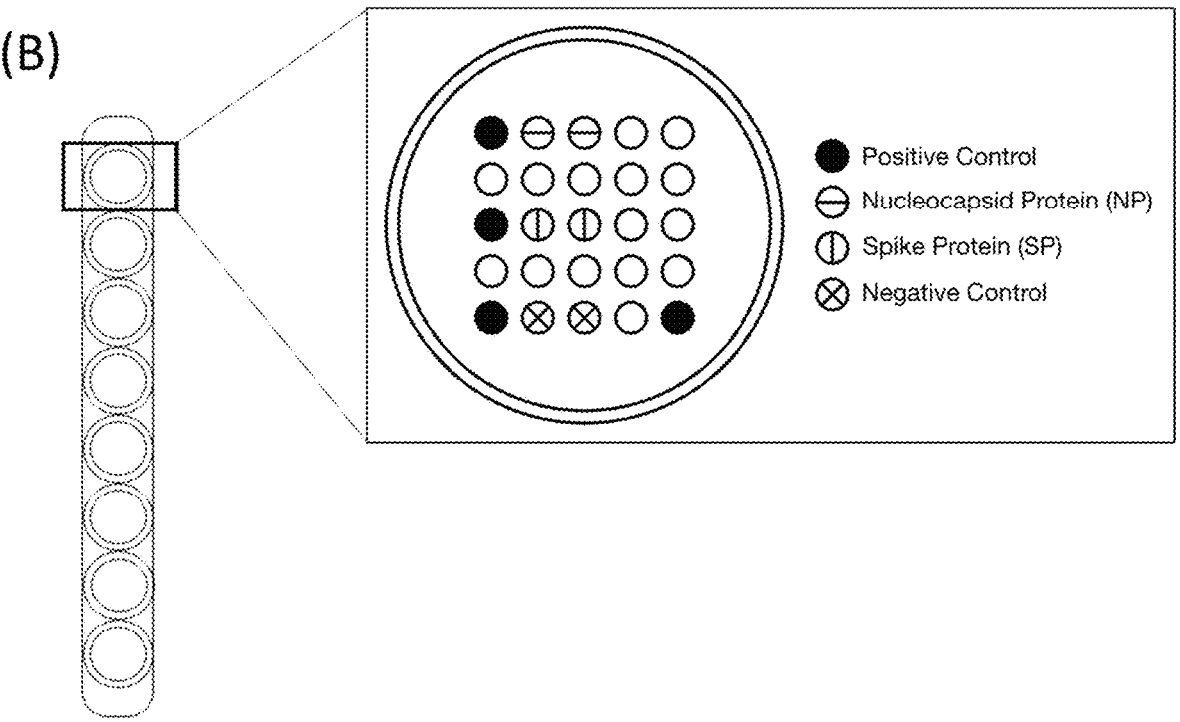

FIG. 10
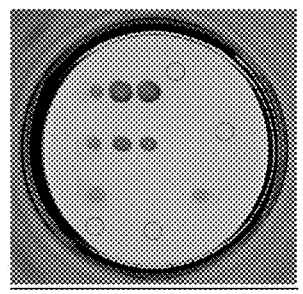
FIGS. 11A-E
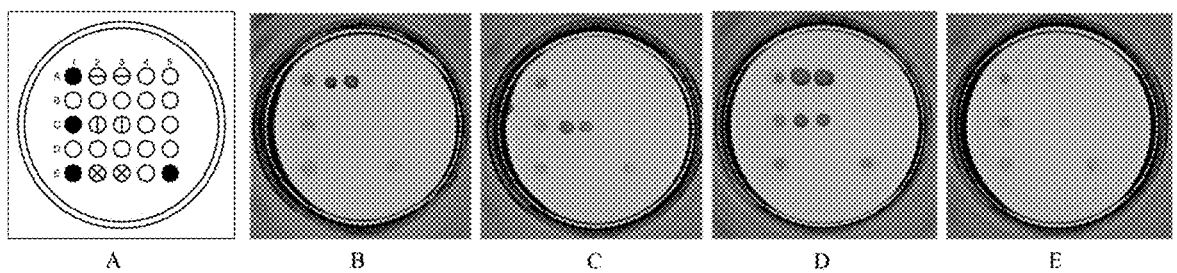
FIG. 12
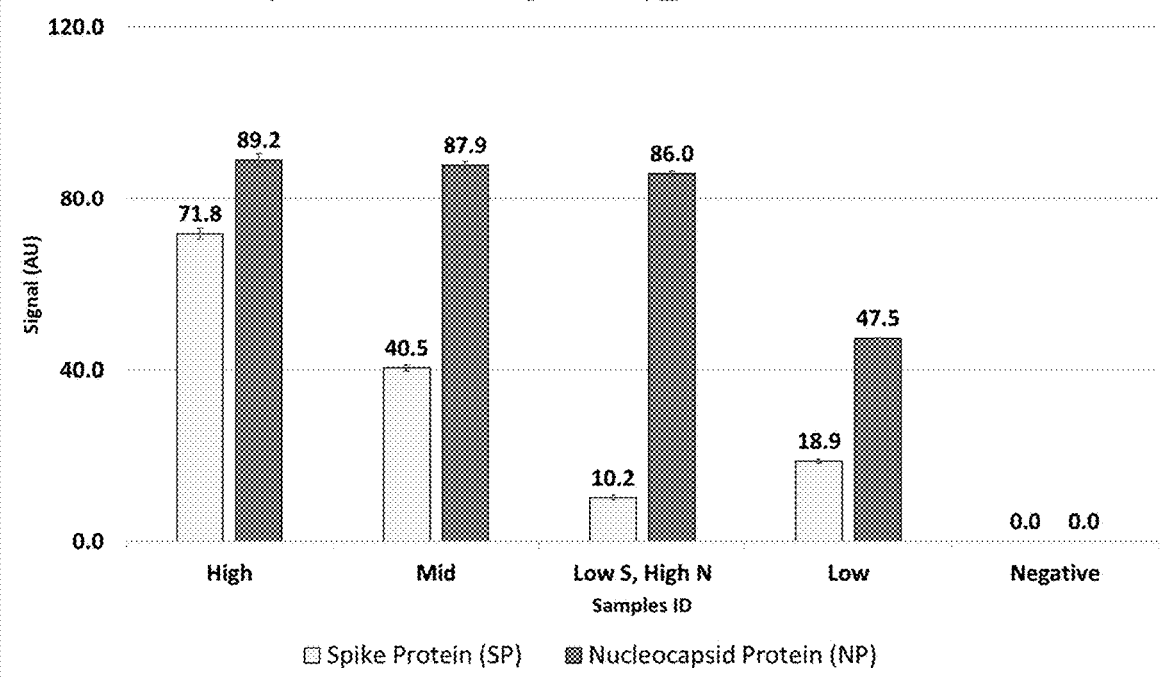

FIGS. 13A-B
(A) 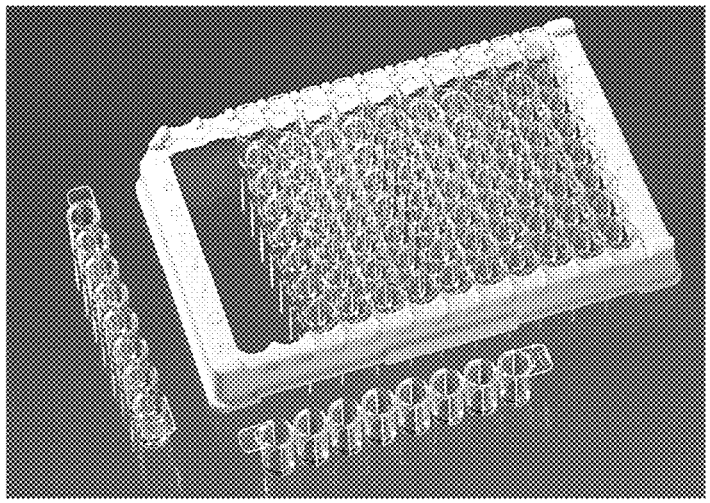
(B) 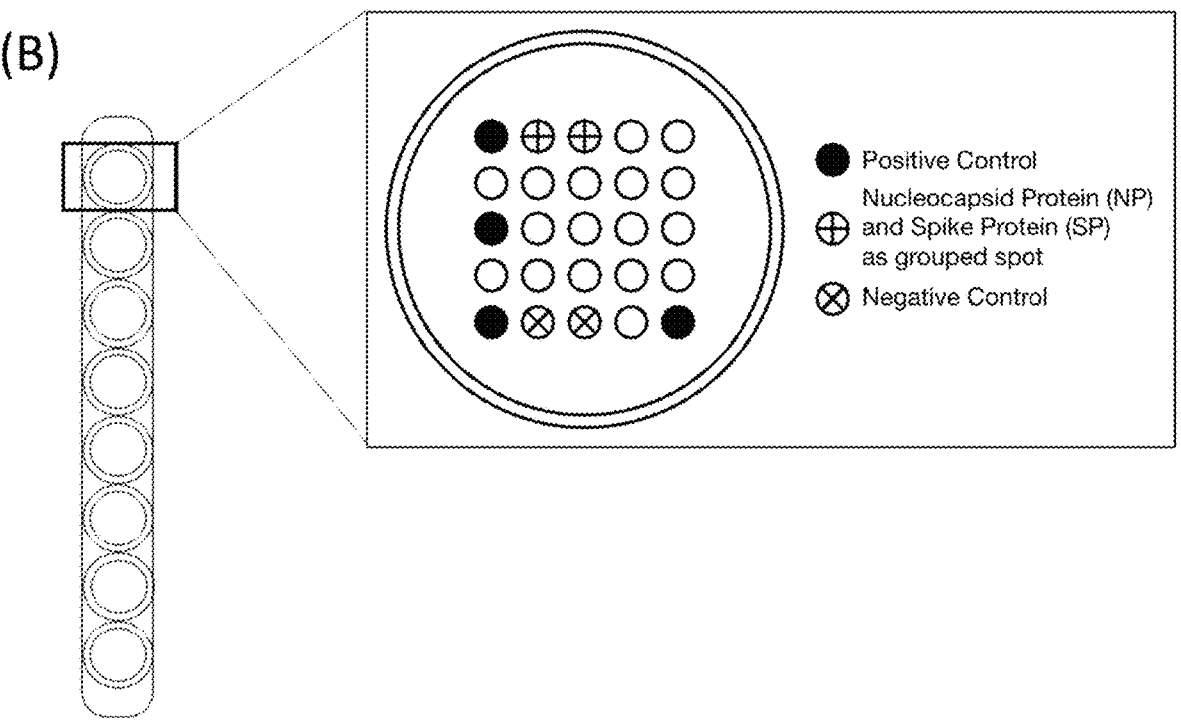

FIG. 14
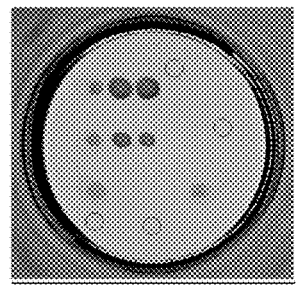
FIGS. 15A-E
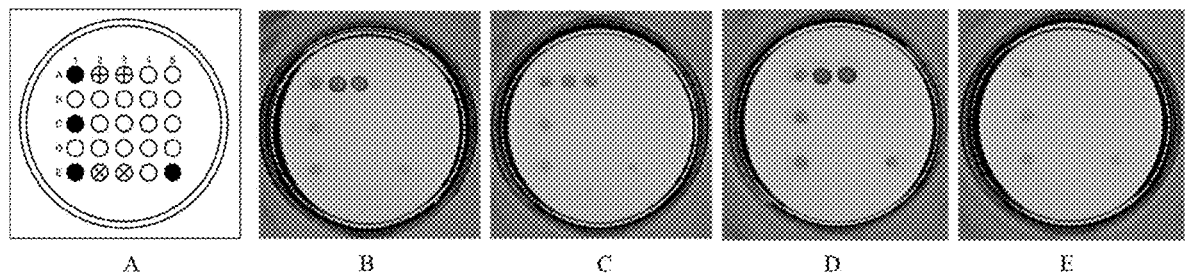
FIG. 16
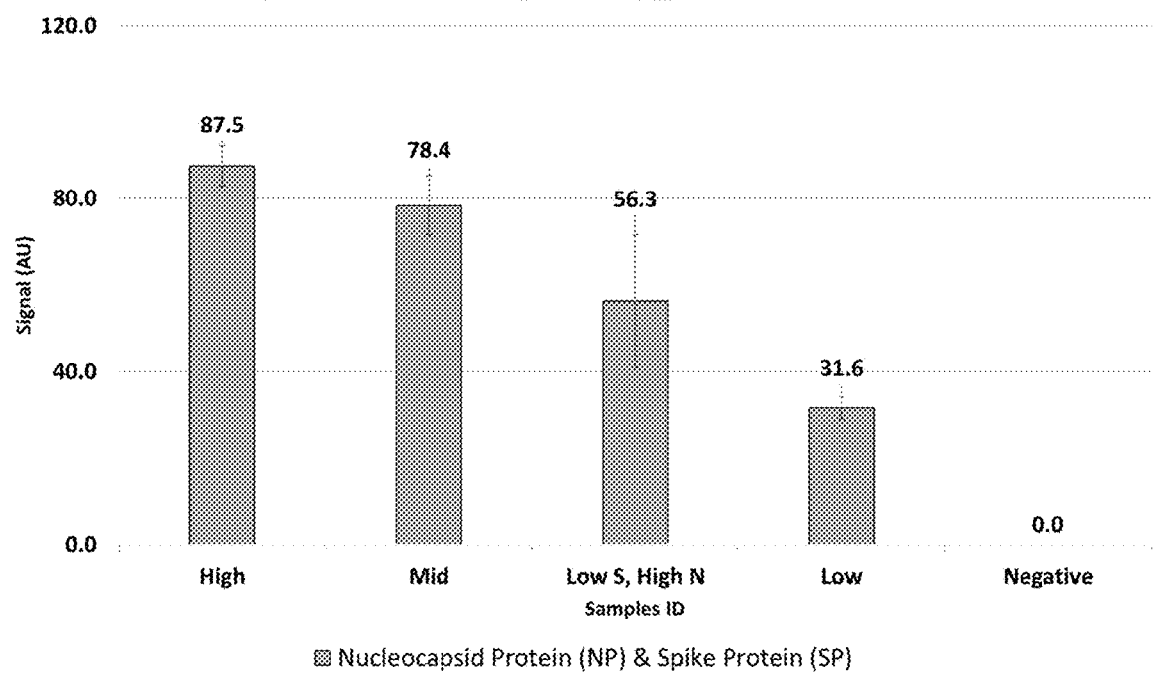

IMMUNOASSAY FOR SARS-COV-2 ANTIBODIES

CROSS-REFERENCE TO RELATED APPLICATIONS

This application is a 35 USC § 371 National Stage application of International Application No. PCT/NZ2021/050116 filed Jul. 29, 2021, now pending which claims the benefit of under 35 USC § 119 (a) to New Zealand Provisional Application Serial No. 766621, filed Jul. 29, 2020. The disclosure of the prior applications are considered part of and are incorporated by reference in the disclosure of this application.

FIELD OF THE INVENTION

The present invention relates generally to multiplex immunoassays and specifically to the detection of SARS-CoV-2 antibodies produced in response to a SARS-CoV-2 infection.

BACKGROUND INFORMATION

Severe acute respiratory syndrome coronavirus 2 (SARS-CoV-2) is the strain of coronavirus that causes coronavirus disease 2019 (COVID-19), the respiratory illness responsible for the COVID-19 pandemic. SARS-CoV-2 is an IV positive-sense single-stranded RNA virus that is contagious in humans.

Each SARS-CoV-2 virion is 50-200 nanometers in diameter. Like other coronaviruses, SARS-CoV-2 has four structural proteins, known as the SP (spike protein), EP (envelope protein), MP (membrane protein), and NP (nucleocapsid protein); the NP holds the RNA genome, and the SP, EP, and MP together create the viral envelope. The spike protein, which has been imaged at the atomic level using cryogenic electron microscopy, is the protein responsible for allowing the virus to attach to and fuse with the membrane of a host cell; specifically, its S1 subunit catalyzes attachment, the S2 subunit fusion.

Protein modeling experiments on the spike protein of the virus soon suggested that SARS-CoV-2 has sufficient affinity to the receptor angiotensin converting enzyme 2 (ACE2) on human cells to use them as a mechanism of cell entry. It has been shown that ACE2 could act as the receptor for SARS-CoV-2. Studies have shown that SARS-CoV-2 has a higher affinity to human ACE2 than the original SARS virus strain. SARS-CoV-2 may also use the protein basigin (CD147) to assist in cell entry.

Initial SP priming by transmembrane protease, serine 2 (TMPRSS2) is essential for entry of SARS-CoV-2. After a SARS-CoV-2 virion attaches to a target cell, the cell's protease TMPRSS2 cuts open the SP of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells. SARS-CoV-2 produces at least three virulence factors that promote shedding of new virions from host cells and inhibit immune response.

There is a need for a rapid and accurate diagnostic test for the detection of antibodies produced against the SARS-CoV-2 virus.

SUMMARY OF THE INVENTION

The present invention is based on the seminal discovery of the use of multiplex immunoassays for detection of infection caused by SARS-CoV-2, e.g., COVID-19. Specifically, the invention provides immunoassays that detect antibodies produced in response to infection by SARS-CoV-2.

In one embodiment, the present invention provides, a substrate with at least two capture elements specific for SARS-CoV-2 on the substrate, each capture element corresponding to and being able to bind a target analyte, the substrate further optionally with a plurality of control elements comprising: at least one fiduciary marker, at least one negative control to monitor background signal, at least one negative control to monitor assay specificity, at least one positive colorimetric control, at least one positive control to monitor assay performance and any combination thereof. In one aspect, the capture elements bind target analytes, wherein the target analytes are indicative of exposure to SARS-CoV-2 and/or COVID-19. In one aspect, the target analyte is an antibody, an antibody fragment, an antibody binding domain, or any combination thereof. In another aspect, the target analyte is a SARS-CoV-2 antibody, fragment or binding domain thereof. In an additional aspect, the capture element is a protein, a protein fragment, a binding protein (BP), a binding protein fragment, an antigen, a virus protein, or any combination thereof. In one aspect, the capture element is a virus structural protein or epitope thereof. In an additional aspect, the virus structural protein or epitope thereof is selected from a SARS-CoV-2 Membrane protein (MP), Nucleocapsid protein (NP), Spike protein (SP), fragment thereof or any combination thereof. In a further aspect, the virus structural protein or epitope thereof is a NP or NP fragment. In one aspect, the substrate is a solid or a porous substrate. In an additional aspect, the solid substrate is a paramagnetic bead, microtiter plate, microparticle, or a magnetic bead. In another aspect, the porous substrate is a membrane.

In an additional embodiment, the present invention provides a kit for detecting a plurality of target analytes in a sample, containing a substrate and optionally one or both of a background reducing reagent, and a colorimetric detection system. In one aspect, the kit also contains one or more items from a wash solution, one or more antibodies for detection of antigens, ligands or antibodies bound to the capture elements or for detection of the positive controls, software for analyzing captured target analytes, and a protocol for measuring the presence of target analytes in samples. In an additional aspect, the antibodies for detection are antibody-binding protein (BP) conjugates, antibody-enzyme label conjugates, or any combination thereof. In a further aspect, the sample is a nasal swab or a blood sample, e.g., serum and/or plasma. In one aspect, the substrate is a solid or a porous substrate. In an additional aspect, the solid substrate is a paramagnetic bead, microtiter plate, microparticle, or a magnetic bead. In another aspect, the porous substrate is a membrane.

In a further embodiment, the present invention provides methods of detecting exposure of a subject to SARS-CoV-2 by contacting a substrate with a biological sample from the subject, wherein the subject is suspected of having COVID-19 or at risk of having COVID-19; and detecting the presence of an antibody that binds to SARS-CoV-2, or a combination thereof, thereby detecting exposure of the subject to SARS-CoV-2. In one aspect, the detection method is a colorimetric, absorbance, chemiluminescence or a fluorescence signal. In certain aspects, the detection method is electrochemical, surface plasmon resonance, localized surface plasmon resonance or interferometry. In an additional aspect, the antibody is IgG. In a further aspect, the sample is a blood sample, e.g., serum and/or plasma.

In another embodiment, the present invention provides methods for processing a microarray by providing a substrate, adding at least one sample to the substrate, and processing the substrate such that a detectable result is given by two or more of at least one fiduciary marker, at least one positive colorimetric control, and at least one positive control to monitor assay performance.

In one embodiment, the present invention provides methods for detecting an analyte in a sample comprising providing a substrate, adding at least one sample to the substrate, and processing the substrate such that a detectable result is provided. In one aspect, the detectable result includes two or more of at least one fiduciary marker, at least one positive colorimetric control, and at least one positive control to detect an analyte in the sample.

BRIEF DESCRIPTION OF THE DRAWINGS

FIG. 1 shows an overview of the COVID-19 multiplex immunoassay (MIA). Indirect immunoassay (IA) for the detection of IgG antibody against SARS-CoV-2.

FIGS. 2A-E show a COVID-19 MIA protocol design. FIG. 2A. Printing of SARS-CoV-2 structural proteins on the assay surface. FIG. 2B. Blocking of assay surface after protein printing. FIG. 2C. Detection of target COVID-19 analytes in the patient sample. FIG. 2D. Detection of specifically bound COVID-19 analytes by binding with HRP-labelled detection Ab against the analytes. FIG. 2E. Generation of colorimetric array spots by the addition of HRP substrate (TMB).

FIGS. 3A-B show a COVID-19 MIA-Membrane-based, Single well assay. FIG. 3A. 16-well platform employing the nitrocellulose membrane as the substrate for the printing of spots. FIG. 3B. Capture antibody against NP and the SARS-CoV-2 structural proteins, i.e. NP, MP, and SP, are printed in duplicate. The positive control spots are printed in the well. The white circles signify that nothing has been printed at that specific position.

FIGS. 4A-B show a COVID-19 MIA-Membrane-based, Single well, using grouped SARS-CoV-2 structural protein assay. FIG. 4A. 16-well platform employing the nitrocellulose membrane as the substrate for the printing of spots. FIG. 4B. Grouped SARS-CoV-2 structural proteins, i.e. NP, MP, and SP, in a mixture are printed in duplicate in the same well. The positive control spots are printed in the well. The white circles signify that nothing has been printed at that specific position.

FIGS. 5A-B show a COVID-19 MIA-Membrane-free, Single well assay. FIG. 5A. 96-well microtiter plate (12 detachable strips of 8 wells each) is used as substrate for the printing of spots. FIG. 5B. Capture Ab against NP and the SARS-CoV-2 structural proteins, i.e. NP, MP, and SP, are printed in duplicate in each well of another strip. The positive control spots are printed in the well. The white circles signify that nothing has been printed at that specific position.

FIGS. 6A-B show a COVID-19 MIA-Membrane-free, Single well, using grouped SARS-CoV-2 structural proteins assay. FIG. 6A. 96-well microtiter plate (12 detachable strips of 8 wells each) is used as substrate for the printing of spots. FIG. 6B. Grouped SARS-CoV-2 structural proteins, i.e. NP, MP, and SP, in a mixture are printed in duplicate in each well of another strip. The positive control spots are printed in all the wells. The white circles signify that nothing has been printed at that specific position.

FIGS. 7A-B show COVID-19 MIA (Membrane-based, Single well assay). FIG. 7A. 16-well platform employing the nitrocellulose membrane as the substrate for the printing of spots.

FIG. 7B. The SARS-CoV-2 structural proteins, i.e., NP and SP, are printed in duplicates.

FIGS. 9A-B show COVID-19 multiplex immunoassay ELISA-based format-conventional 96 wells ELISA plate (12 strips of 8 wells each)-membrane free. FIG. 9A. Conventional 96 wells ELISA plate. FIG. 9B. NP and SP SARS-CoV-2 proteins printed in duplicate.

FIG. 10 shows Wells' regions used to calculate the assay background. The assay background was calculated as a median of the intensity obtained across the region inside the dark circles.

FIGS. 11A-E show the printing layout and wells at the end of an assay. FIG. 11A. Printing layout. FIG. 11B. Assay run using Anti-N Protein reconstructed human mAb, IgG at 1 µg/ml as a sample. FIG. 11C. Assay run using Anti-Spike-RBD human reconstructed mAb, IgG at 1 µg/ml as a sample. FIG. 11D. Assay run using a sample (Panel #18) which is reactive for both SARS-CoV-2 Nucleocapsid Protein and SARS-CoV-2 Spike Glycoprotein (S1). FIG. 11E. Assay run using a sample (Panel #34) which is non-reactive for both printed antigens. The visible signal at SARS-CoV-2 NP spots is the highest background observed across all the non-reactive samples tested.

FIG. 12 shows an assessment of First WHO International Reference Panel for anti-SARS-CoV-2 Immunoglobulin using the COVID-19 MIA-membrane free, single well format.

FIGS. 13A-B show COVID-19 multiplex immunoassay ELISA-based format-96 wells ELISA plate (12 strips of 8 wells each)-membrane free. FIG. 13A. Conventional 96 wells ELISA plate. FIG. 13B. NP and SP SARS-CoV-2 proteins are mixed then printed in duplicate.

FIG. 14 shows the Wells' regions used to calculate the assay background. The assay background was calculated as a median of the intensity obtained across the region inside the dark circles.

FIGS. 15A-E show printing layout and wells at the end of an assay. FIG. 15A. Printing layout. FIG. 15B. Assay run using Anti-N Protein reconstructed human mAb, IgG at 1 µg/ml as sample. FIG. 15C. Assay run using Anti-Spike-RBD human reconstructed mAb, IgG at 1 µg/ml as sample. FIG. 15D. Assay run using a sample (Panel #18) which is reactive for both SARS-CoV-2 Nucleocapsid Protein and SARS-CoV-2 Spike Glycoprotein (S1). FIG. 15E. Assay run using a sample (Panel #34) which is non-reactive for both printed antigens. The visible signal at SARS-CoV-2 NP&SP mixed spots is the highest background observed across all the non-reactive samples tested.

FIG. 16 shows an assessment of First WHO International Reference Panel for anti-SARS-CoV-2 Immunoglobulin using the COVID-19 MIA-membrane free, single well, using grouped SARS-CoV-2 structural proteins format.

DETAILED DESCRIPTION OF THE INVENTION

Figure 8:
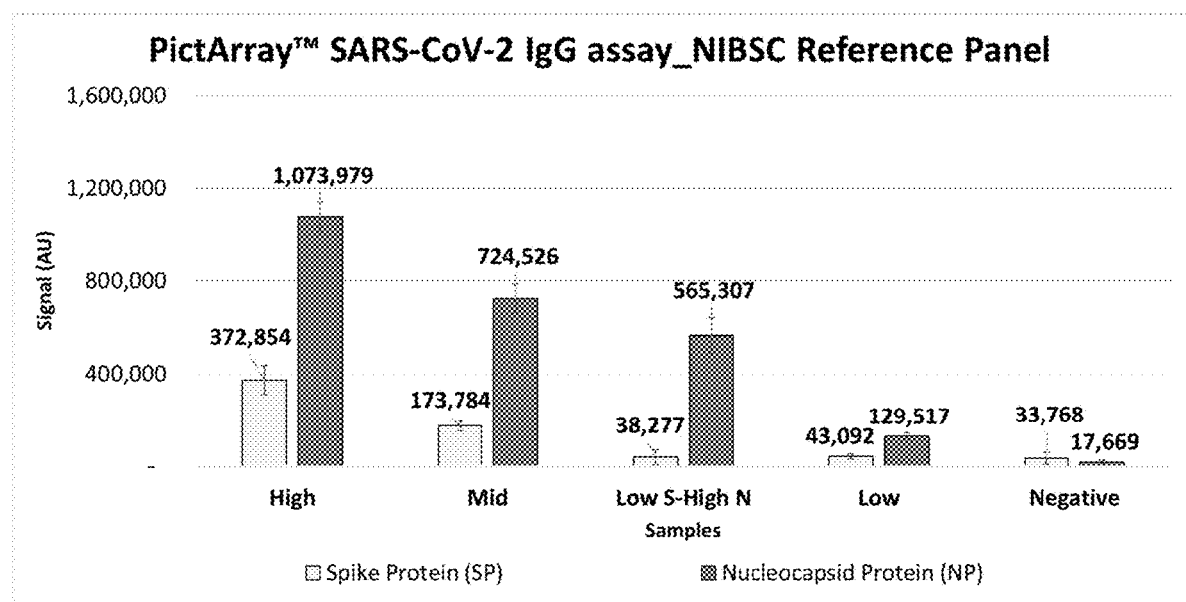
FIG. 8 shows an assessment of First WHO International Reference Panel for anti-SARS-CoV-2 Immunoglobulin using the COVID-19 MIA.

The present invention is based on the seminal discovery of the use of multiplex immunoassays for detection of antibodies produced in response to infection by SARS-CoV-2.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein, which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The present invention enables the in vitro diagnosis of COVID-19 by detection of antibodies produced against SARS-CoV-2 via a multiplex immune assay (MIA). Therefore, COVID-19 is diagnosed at a very early-stage starting from about 3 days from the onset of infection when nucleocapsid protein (NP) is shed in patients. The peak levels of NP have been observed in humans at about 10 days after onset of infection, which continuously decreases in the patients and becomes undetectable. The seroconversion of antibodies (IgG) against SARS-CoV-2 has been shown to occur between about 16-23 days from the onset of infection.

In one embodiment, the present invention provides, a substrate with at least two capture elements specific for SARS-CoV-2 on the substrate, each capture element corresponding to and being able to bind a target analyte, the substrate further optionally with a plurality of control elements comprising at least one fiduciary marker, at least one negative control to monitor background signal, at least one negative control to monitor assay specificity, at least one positive colorimetric control, at least one positive control to monitor assay performance and any combination thereof. In one aspect, the capture elements bind target analytes, wherein the target analytes are indicative of COVID-19. In another aspect, the target analyte is a SARS-CoV-2 antibody, fragment or binding domain thereof. In an additional aspect, the capture element is a protein, a protein fragment, a binding protein (BP), a binding protein fragment, an antigen, an antigenic determinant, a virus protein, or any combination thereof. In one aspect, the capture element is a virus structural protein or epitope thereof. In an additional aspect, the virus structural protein or epitope thereof is selected from a SARS-CoV-2 Membrane protein (MP), Nucleocapsid protein (NP), Spike protein (SP), or any combination thereof. In a further aspect, the virus structural protein or epitope thereof is a NP or NP fragment. In one aspect, the substrate is a solid or a porous substrate. In an additional aspect, the solid substrate is a paramagnetic bead, microtiter plate, microparticle, or a magnetic bead. In another aspect, the porous substrate is a membrane.

As used herein, the term "substrate" is any surface that supports an immunoassay. The substrate of the invention may be a solid substrate or a porous substrate, for example.

In certain aspects, the substrate is a solid substrate. Examples of solid substrates include, but are not limited to, 96 well microtiter plate, glass, microbeads, nano/microparticles and magnetic beads. In one aspect, a 96 well microtiter plate is polystyrene, PDMS, PMMA, polycarbonate, cyclic polyolefins, Zeonor, Zeonex, or cellulose acetate. In various aspects, the solid substrate maybe glass beads, nano-/microparticles, magnetic beads or paramagnetic beads.

In some aspects, the porous substrate is a membrane. The term "porous membrane" refers to a membrane with protein binding characteristics and a narrow pore-size distribution (e.g,. microporous). In one embodiment, the porosity of the membrane may determine the exposure time of reagents with membrane bound components by controlling the flow rate through the membrane. Microporous membranes for use in the present invention include by way of example, nitrocellulose, nylon, polyvinylidene difluoride, polyester, polystyrene, polyethersulfone, cellulose acetate, mixed cellulose esters and polycarbonate. For example, PictArray™ (U.S. Pat. No. 9,625,453)

The choice of membrane is typically dependent on three main membrane characteristics: protein-binding capacity, porosity, and strength. The ability of the membrane to immobilize macromolecules, in particular proteins, is important as the membrane serves as the solid phase used in the assay. However, this ability must be balanced with the availability of appropriate reagents (for example, blockers) for blocking non-specific interactions on the membrane. Similarly, in a flow-through configuration, the porosity of the membrane may determine the exposure time of reagents with membrane bound components by controlling their flow rate through the membrane. However, porosity must be balanced with the degree of array spot spreading during array manufacture, which can result in decreased signal intensity or cross contamination between adjacent spots. The strength of the membrane is important for the manufacture and eventual use of a device. A wide range of membranes are available with differing characteristics, allowing a particular membrane to be chosen depending on the requirements of an assay.

In preferred embodiments, microporous membranes for use in the present invention comprise nitrocellulose, nylon, polyvinylidene difluoride, polyester, polystyrene, polyethersulfone, cellulose acetate, mixed cellulose esters and polycarbonate.

While some membranes such as cellulose acetate may have insufficient binding capacities for diagnostic immunoassays, the characteristics of such membranes may be applicable for assays where lower levels of accuracy or sensitivity are sufficient.

The microporous membrane is removably attachable to a bottomless microtiter plate for example. Accordingly, the membrane can be divided into individual microtiter wells that are separated from each other by a physical barrier, to prevent sample mixing between wells. Moreover, different assays can be conducted in separate wells, requiring smaller volumes of assay reagents.

The assay elements (control and capture elements) are placed on the substrate surface, with or without an adapter molecule between the membrane and the element. Preferably, the assay elements bind to the substrate by covalent or non-covalent interaction. One of skill in the art will recognize that methods of placing assay elements on the substrate include printing, spotting or other techniques known in the art. For purposes of the present application, the term "printing" can be used to include any of the methods for placing the assay elements on a membrane.

The terms "array" or "microarray" as used herein refer to a collection of multiple assay elements on a substrate. Specifically, an array is a collection of capture elements and/or control elements on a substrate.

In various aspects, the elements on the array are placed on the substrate in discrete areas of between 100 μm to 500 μm in diameter. More preferably, the discrete areas are between 350 μm to 400 μm in diameter. In certain aspects, the discrete areas of the array are placed in a 5×5 grid. In one aspect, the array comprises up to nine control elements and two replicates of each of eight different capture elements. In one aspect, the capture elements are printed in two or more replicates of four different capture elements and multiples thereof.

As used herein, the term "assay element" refers to any of a number of different elements for use in an array of the invention. Exemplary assay elements include, but are not limited to, capture elements and control elements.

The term "capture element" refers to a molecule that is able to bind to a target analyte. Examples of useful capture elements include proteins, protein fragments, polypeptides, polypeptide fragments, binding proteins, binding protein fragments, antibodies (polyclonal, monoclonal, or chimeric), antibody fragments, antibody heavy chains, antibody light chains, single chain antibodies, single-domain antibodies (a VHH for example), Fab antibody fragments, Fc antibody fragments, Fv antibody fragments, F(ab')2 antibody fragments, Fab' antibody fragments, single-chain Fv (scFv) antibody fragments, antibody binding domains, antigens, antigenic determinants, epitopes, haptens, immunogens, immunogen fragments, binding domains, a metal ion, a metal ion-coated molecule, biotin, avidins, streptavidins; substrates, enzymes, abzymes, co-factors, receptors, receptor fragments, receptor subunits, receptor subunit fragments, ligands, inhibitors, hormones, binding sites, lectins, polyhistidines, coupling domains, oligonucleotides, and a virus protein. Useful capture elements will correspond to and be able to bind a specific target analyte, such as a molecule or class of molecules that are present in a sample to be tested.

In one embodiment, the capture element is selected from a protein, a protein fragment, a binding protein, a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab')2 antibody fragment, a Fab' antibody fragment, a single-chain Fv (scFv) antibody fragment, an antibody binding domain, an antigen, an antigenic determinant, an epitope, a hapten, an immunogen, an immunogen fragment, a binding domain; metal ion, or metal ion-coated molecule, biotin, avidin, streptavidin; a substrate, an enzyme, an abzyme, a co-factor, a receptor, a receptor fragment, a receptor subunit, a receptor subunit fragment, a ligand, an inhibitor, a hormone, a binding site, a lectin, a polyhistidine, a coupling domain, an oligonucleotide, a viral protein or a combination of any two or more thereof.

Specifically, the capture element can be a SARS-CoV-2 viral structural protein. SARS-CoV-2 structural proteins include nucleocapsid protein (NP), membrane protein (MP), spike protein (SP), or epitopes thereof. The capture element may be NP/MP/SP or a fragment of NP/MP/SP.

As used herein, the terms "biomarker" refers to any substance used as an indicator of a biologic state. Thus, a biomarker can be any substance whose detection indicates a particular disease state (for example, the presence of an antibody may indicate a prior infection). Furthermore, a biomarker can be indicative of a change in expression or state of a protein that correlates with the risk or progression of a disease, or with the susceptibility of the disease to a given treatment. Once a proposed biomarker has been validated, it can be used to diagnose disease risk, presence of disease in an individual, or to tailor treatments for the disease in an individual (e.g., choices of drug treatment or administration regimes). In evaluating potential drug therapies, a biomarker may be used as a surrogate for a natural endpoint such as survival or irreversible morbidity. If a treatment alters the biomarker, which has a direct connection to improved health, the biomarker serves as a "surrogate endpoint" for evaluating clinical benefit. In one aspect, the target analyte is a biomarker.

In one embodiment, the target analyte is selected from a protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, a virus protein, a virus coat protein, a virus, a virus protein or epitope thereof or any combination of any two or more thereof.

In one aspect, the target analyte is a SARS-CoV-2 antibody, antibody fragment or binding domain thereof.

Capture elements specific for a target analyte are used to detect the presence or absence of the analyte in a sample. A wide range of complementary binding or coupling partners are known, with the choice of capture elements determined by the analytes to be detected, the requirement for adapter molecules and the level of specificity required for the assay. In various aspects, the capture elements are specific for binding/detecting IgG antibodies produced by a SARS-CoV-2 infection.

The term "control element" refers to an element that is used to provide information on the function of the assay, for example binding specificity, the level of non-specific background binding, the degree of binding cross-reactivity, and the performance of assay reagents and the detection system. Preferred controls useful herein include at least one negative control to monitor background signal, at least one negative control to monitor assay specificity, at least one positive colorimetric control, and at least one positive control to monitor assay performance.

The substrate of the invention comprises at least one fiduciary marker that will always be detectable on the substrate, preferably detectable irrespective of the performance of the assay or processing of the substrate.

The term "fiduciary marker" refers to a colored marker or label that will always be detectable on the substrate, preferably irrespective of the performance of the assay or processing of the substrate. The use of at least one fiduciary marker will obviate the necessity of this element being detected based on successful array processing, in comparison to the positive colorimetric controls. The fiduciary marker is therefore a "true" positive control that would always be detectable regardless of array processing, and can be used to orient and help to grid the array.

In preferred aspects, the fiduciary marker is a dye, dye-conjugated protein or a chromogenic protein such as hemoglobin.

The term "negative control" refers to an element comprising print buffer or an unrelated protein to which no complementary binding partner is intended to be present in the assay. Any detectable signal from the negative control can be used to determine the background threshold of the assay and the accuracy of any positive results. In one aspect, the negative control to monitor background signal is print buffer. The print buffer is a solution used to carry and print the capture elements and control elements onto the substrate and may comprise buffered saline, glycerol and a surfactant, preferably a polysorbate surfactant such as Tween 20. The blocking solution is used to reduce non-specific protein binding to the substrate surface and preferably comprises skim milk, casein, bovine serum albumin, gelatins from fish, pigs or other species, dextran or any mixture of any two or more thereof, preferably in a solution of phosphate buffered saline and a surfactant such as Tween 20.

The term "control capture element" refers to a capture element that functions as a control, either a negative control that should not bind any analyte or a positive control that will bind a non-target analyte.

The substrate of the invention also comprises at least one control to monitor assay performance. The control is intended to provide information of the efficiency of the complementary binding interactions or the quality or performance of the reagents used.

The term "control to monitor assay performance" refers to an element that forms one part of a complementary binding interaction during an assay and is intended to provide information on the accuracy of the assay result. In one embodiment, the positive control to monitor assay performance comprises one binding partner of a complementary binding pair, where the other binding partner is a sample component or an assay reagent. The assay performance control is preferably selected from a target analyte, a binding partner corresponding to and able to bind a non-target analyte that will be present in the sample, a binding partner corresponding to and able to bind an assay reagent, and a colorimetric enzyme label, or any combination of any two or more thereof. An example of a binding partner corresponding to and able to bind a non-target analyte that will be present in the sample is an anti-Ig antibody that will bind an immunoglobulin present in a serum sample, therefore confirming a sample has been added. An example of a binding partner corresponding to and able to bind an assay reagent is an anti-Ig antibody that will bind a secondary immunoglobulin that is used to process the assay, such as biotinylated anti-target analyte antibody. Another example of a binding partner corresponding to and able to bind an assay reagent is a biotinylated antibody that will bind a streptavidin-peroxidase conjugate that is used to process the assay.

In one aspect, the assay performance control comprises one binding partner of a complementary binding pair, wherein the other binding partner is an assay reagent. The assay performance control is preferably selected from the list comprising the target analyte, a non-specific binding partner or a colorimetric enzyme label.

In another aspect, the complementary binding partners comprise antibody-antigen interactions or antibody-ligand interactions.

The substrate of the invention also comprises at least one control to monitor assay specificity. The control is intended to provide information of the specificity of binding between the capture element and the target analyte, or between the binding partners of the assay detection steps.

The term "control to monitor assay specificity" refers to an element that is closely related to at least one binding partner of a complementary binding pair present in the assay and is intended to provide information of the specificity of the complementary binding. This control is a negative control that is not expected to generate a detectable result during normal assay processing. For example, in an antigen array for antibody detection, the assay specificity control would comprise an antigen that should not bind any antibody in the sample.

In one aspect, the assay specificity control comprises one or more antibody isotypes, a corresponding antibody or antibody isotype from a different animal species or a closely related ligand. For example, in human antibody arrays, human IgG and anti-human IgG can be used as controls to monitor assay specificity.

The term "positive colorimetric control" as used herein refers to an enzyme or enzyme conjugate that provides a detectable signal upon addition of the enzyme substrate.

In one embodiment, the positive colorimetric control is an enzyme label conjugate capable of reacting with a colorimetric substrate, comprising an enzyme selected from the list comprising horseradish peroxidase, alkaline phosphatases, β-D-galactosidase or glucose oxidase.

The identity of the assay controls will be dependent on the type of array, the identity of the target analyte, and the type of sample to be analyzed.

For example, either anti-human IgG-HRP or anti-mouse IgG-HRP may be used in arrays printed with antigens and antibodies, respectively. The final detection antibody in antigen arrays will often be anti-human IgG-HRP, while for antibody arrays it will often be a biotinylated mouse IgG. These controls can provide a positive control in addition to providing information on the performance or quality of the HRP substrate.

Mouse IgG, human IgG and anti-human IgG present on antigen or antibody arrays can act either as positive or negative controls depending on the array format, in addition to providing information of assay specificity. For example, mouse IgG should provide the positive signal in antibody arrays, while the latter two should provide a positive signal in antigen arrays. These controls can also serve as controls for overall assay performance.

The terms "sample" and "specimen" as used herein are used in their broadest sense to include any composition that is obtained and/or derived from biological or environmental source, as well as sampling devices (e.g., swabs) which are brought into contact with biological or environmental samples. "Biological samples" include body fluids such as urine, blood, plasma, fecal matter, cerebrospinal fluid (CSF), and saliva. In one embodiment, the biological sample is a cell, tissue, and or fluid obtained from a mammal, including from the upper respiratory tissues (such as nasopharyngeal wash, nasopharyngeal aspirate, nasopharyngeal swab, and oropharyngeal swab), from the lower respiratory tissues (such as bronchiolar lavage, tracheal aspirate, pleural tap, sputum), blood, plasma, serum, and stool. These examples are illustrative, and are not to be construed as limiting the sample types applicable to the present invention.

In various aspects of the present invention, the sample is a blood sample, including a plasma or serum sample.

The assay techniques used in conjunction with the substrates of the present invention include any of a number of well-known colorimetric enzyme-linked assays. Examples of such systems are well known in the art. The assay techniques are based upon the formation of a complex between a complementary binding pair, followed by detection with a colorimetric detection system comprising an enzyme-conjugate label and a colorimetric substrate. The detection system will be described with reference to enzyme-linked immunosorbent assays (ELISA), though a skilled person would appreciate that such techniques are not restricted to the use of antibodies but are equally applicable to any colorimetric assay.

In one embodiment, the ELISA is in the "sandwich" assay format. In this format, the target analyte to be measured is bound between two antibodies—the capture antibody and the detection antibody. In another embodiment, the ELISA is a non-competitive assay, in which an antibody binds to the capture antigen and the amount of bound antibody is determined by a secondary detection antibody.

Either monoclonal or polyclonal antibodies may be used as the capture and detection antibodies in sandwich ELISA systems. Monoclonal antibodies have an inherent monospecificity toward a single epitope that allows fine detection and quantitation of small differences in antigen. A polyclonal antibody can also be used as the capture antibody to bind as much of the antigen as possible, followed by the use of a monoclonal antibody as the detecting antibody in the sandwich assay to provide improved specificity. A monoclonal antibody can also be used as the capture antibody to provide specific analyte capture, followed by the use of a polyclonal antibody as the detecting antibody in the sandwich assay. Additionally, both the capture and the detection antibodies could be monoclonal.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275-1281, 1989, which is incorporated herein by reference). These and other methods of making, for example, chimeric, humanized, CDR-grafted, single chain, and bifunctional antibodies are well known (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1999); Hilyard et al., Protein Engineering: A practical approach (IRL Press 1992); Borrabeck, Antibody Engineering, 2d ed. (Oxford University Press 1995); each of which is incorporated herein by reference). In addition, modified or derivatized antibodies, or antigen binding fragments of antibodies, such as pegylated (polyethylene glycol modified) antibodies, can be useful for the present methods. As such, Fab, F(ab')2, Fd and Fv fragments of an antibody that retain specific binding activity are included within the definition of an antibody.

The term "secondary antibody" refers to an antibody that will bind a target analyte and that is conjugated with either an adaptor molecule such as biotin or an enzyme label such as horseradish peroxidase (HRP). Antibody-adaptor conjugates are processed to give a detectable result by contacting the antibody-adaptor conjugate with an adaptor-enzyme conjugate and then the enzyme substrate; for example, antibody-biotin conjugates will bind streptavidin-HRP conjugates. Antibody-enzyme label conjugates include antibody-HRP conjugates. Use of secondary antibodies is discussed and exemplified below.

The term "binds specifically" or "specific binding activity" or the like, means that two molecules form a complex that is relatively stable under physiologic conditions. The term is also applicable where, an antigen-binding domain is specific for a particular epitope, which is carried by a number of antigens, in which case the antibody carrying the antigen-binding domain will be able to bind to the various antigens carrying the epitope. Specific binding is characterized by a high affinity and a low to moderate capacity. Typically, the binding is considered specific when the affinity constant is about $1\times10^{-6}$ M, generally at least about $1\times10^{-7}$ M, usually at least about $1\times10^{-8}$ M, and particularly at least about $1\times10^{-9}$ M or $1\times10^{-10}$ M or less.

After array manufacture and prior to sample addition, all available protein-binding sites on the substrate surface are blocked by addition and incubation with one or a combination of reagents. These reagents are called "Blockers" and serve to decrease or at best eliminate non-specific protein binding from the sample on the substrate surface thereby decreasing overall background signal. This increases the ratio of signal to noise, thereby increasing the overall sensitivity of the assay. Blockers play no active part in the subsequent reactions between the sample and other assay reagents and the immobilized proteins on the substrate. Exemplary blockers include, but are not limited to, bovine serum albumin, casein, non-fat dry milk, gelatin derived from fish, pigs and other sources, dextran, serum derived from sources other than the sample being analyzed such as from steelhead salmon, guinea pigs, hamsters, rabbit and other sources, polyethylene glycol, polyvinyl pyrrollidone, and commercial preparations including HeteroBlock (Omega Biologicals, Bozeman, Mont.), SuperBlock, StartingBlock, SEA BLOCK (Pierce, Rockford, Ill.). Typically, blockers are made up in buffer solutions such as, for example, phosphate buffer, phosphate buffered saline, Tris buffer, acetate buffer and others. The blockers may also be supplemented with detergents such as, for example, Tween 20, Tween 80, Nonidet P40, sodium dodecyl sulfate and others.

An important consideration in designing an array is that the capture and detection antibodies of each binding pair must recognize two non-overlapping epitopes so that when the antigen binds to the capture antibody, the epitope recognized by the detection antibody must not be obscured or altered. A large number of complementary binding pairs have already been developed for ELISA and can be used in the present invention.

For multiplexed assays, it is also important that there is no overlap between each of the binding pairs to eliminate cross-reactivity. A number of multiplexed ELISAs have been developed and it is anticipated other combinations of binding pairs could be configured through testing.

In one aspect, the enzyme-conjugate label comprising an enzyme selected from the list comprising horseradish peroxidase, alkaline phosphatase, β-D-galactosidase or glucose oxidase.

In an additional aspect, the enzyme label may be conjugated directly to a primary antibody or introduced through a secondary antibody that recognizes the primary antibody. It may also be conjugated to a protein such as streptavidin if the primary antibody is biotin labelled.

In a further aspect, the assay detection system comprises a detection colorimetric substrate selected from the list comprising 3,3',5,5'-tetramethylbenzidine, diaminobenzidine, metal-enhanced diaminobenzidine, 4-chloro-1-naphthol, colloidal gold, nitro-blue tetrazolium chloride, 5-bromo-4-chloro-3'-indolylphosphate p-toluidine salt and naphthol AS-MX phosphate+Fast Red TR Salt.

In certain aspects, the colorimetric reaction can be detected and optionally quantified and analyzed using an image capture device such as a digital camera or a desktop scanner attached to a computer. Known methods for image analysis may be used. For example, the concentration values of known standard elements can be used to generate standard curves. Concentration values for unknown analytes can be analyzed using the standard curve for each analyte to calculate actual concentrations. Values for each analyte can be identified based on the spotting position of each capture element within the array.

The substrates of the present invention are particularly amenable to use in kits for the detection of target analytes. Such kits may comprise the substrates together with instructions and any assay consumables required. Different kits are envisaged for different target analytes and types of array. Accordingly, in an additional embodiment, the present invention provides a kit for detecting a plurality of target analytes in a sample, containing a substrate and optionally one or both of a background reducing reagent, and a colorimetric detection system. In one aspect, the kit also contains one or more items from a wash solution, one or more antibodies for detection of antigens, ligands or antibodies bound to the capture elements or for detection of the positive controls, software for analyzing captured target analytes, and a protocol for measuring the presence of target analytes in samples. In an additional aspect, the antibodies for detection are antibody-binding protein (BP) conjugates, antibody-enzyme label conjugates, or any combination thereof. In a further aspect, the sample is a blood sample, e.g., serum or plasma. In one aspect, the substrate is a solid or a porous substrate. In an additional aspect, the solid substrate is a paramagnetic bead, microtiter plate, microparticle, or a magnetic bead. In certain aspects, the porous substrate is a membrane.

In another aspect, the invention also relates to a method of processing a substrate of the invention. Such a method comprises providing a substrate of the invention as described above, adding at least one sample to the substrate, and processing the substrate such that a detectable result is given by two or more of at least one fiduciary marker, at least one positive colorimetric control, and iii) at least one positive control to monitor assay performance.

In another aspect, the present invention provides methods for processing a microarray by providing a substrate, adding at least one sample to the substrate, and processing the substrate such that a detectable result is given by two or more of at least one fiduciary marker, at least one positive colorimetric control, and at least one positive control to monitor assay performance.

In one aspect, the step of processing the substrate or microarray comprises a blocking step during which available protein-binding sites on the substrate or microarray are blocked with a blocker, an optional wash step, contacting the substrate or microarray with the sample containing the one or more analytes to be measured, a wash step to remove non-bound material from the substrate or microarray, contacting the substrate or microarray with one or more secondary antibodies that correspond to and will bind one or more target analytes and non-target analyte that is bound to an assay performance control, a wash step, and contacting the substrate or microarray with one or both of an enzyme conjugate or an enzyme substrate to generate a detectable result.

In one embodiment, the present invention provides methods for detecting an analyte in a sample comprising providing a substrate, adding at least one sample to the substrate, and processing the substrate such that a detectable result is provided. In one aspect, the detectable result includes two or more of at least one fiduciary marker, at least one positive colorimetric control, and at least one positive control to detect an analyte in the sample.

In another aspect, the substrate of the invention can be used for the simultaneous detection of at least one target analyte in a sample, and preferably a plurality of different target analytes in a sample, and have utility in diagnostic and screening assays.

Thus, the substrates of the invention provide the advantage that they can be adapted to high throughput (or ultra high throughput) analysis and, therefore, any number of samples (e.g., 96, 1024, 10,000, 100,000, or more) can be examined in parallel, depending on the particular support used. A particular advantage of adapting the substrates to high throughput analysis is that an automated system can be used for adding or removing reagents from one or more of the samples at various times, for adding different reagents to particular samples, or for subjecting the samples to various heating cycles.

For example, the automated system may consist of one or more temperature-controlled chambers and one or more robotic arms mounted on a deck that has platforms configured to hold 96-well plates. The movement of the robotic arms and the temperature in the chambers are controlled by a central computer unit. The array plates are stacked on the deck of the instrument. In one embodiment, the plates containing samples to be analyzed are stacked in a chamber with temperature of 4° C. One robotic arm then sequentially transfers each individual array plate on one platform while the other arm sequentially transfers each individual sample plate on the second platform. A nozzle containing 96 disposable tips then aspirates a predetermined volume of sample from each well of the sample plate and transfers the sample to the corresponding wells of the array plate. The array plate containing the sample is then transferred to a chamber with temperature of 37° C. This process is repeated until sample has been added to all the array plates stacked on the deck. The array plates are incubated for a predetermined time followed by transfer of each plate to the platform for addition of wash buffer with the nozzle containing 96 disposable tips. The wash buffer is aspirated after a predetermined time and this wash process is repeated multiple (i.e., two or more) times. Each array plate then receives the secondary antibody followed by transfer to a chamber with temperature of 37° C. The array plates are incubated for a predetermined time followed by transfer of each plate to the platform for addition of wash buffer with the nozzle containing 96 disposable tips. The wash buffer is aspirated after a predetermined time and this wash process is repeated multiple (i.e., two or more) times. Each array plate then receives the detection reagent followed by incubation for a predetermined time followed by transfer of each plate to the platform for addition of wash buffer with the nozzle containing 96 disposable tips. The wash buffer is aspirated after a predetermined time and the plate transferred to the 37° C. chamber for drying. The plates are transferred back to the deck after a predetermined period and manually processed for analyses of data.

In addition to the convenience of examining multiple test agents and/or samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

In a further embodiment, the present invention provides methods of detecting exposure of a subject to SARS-CoV-2 by contacting a substrate with a biological sample from the subject, wherein the subject is suspected of having COVID- 19; and detecting the presence of an antibody that binds to SARS-CoV-2. In one aspect, the detection method is automated, manual, lateral flow, solid-phase, chemiluminescence, microfluidics, lab-on-a-chip based immunoassay, ELISA, or a combination thereof. In an additional aspect, the antibody is IgG. In a further aspect, the sample is a blood sample, for example serum or plasma.

The present invention provides methods of in vitro diagnostic applications for the detection of antibodies produced in response to SARS-CoV-2 infection such as manual multiplex immune assay, automated multiplex immune assay (MIA), manual singleplex ELISA (solid phase), automated chemiluminescent immune assay (CLIA), wash-free immune assays (manual and automated), automated centrifugal microfluidics-based immunoassay, lab-on-a-chip based immunoassay, paramagnetic bead-based manual ELISA, manual paper-based ELISA, Point-of-care (POC) immunoassays and other immunoassay formats. In one aspect, detection is by colorimetric imaging (e.g., PictArray™, U.S. Pat. No. 9,625,453), absorbance (e.g., manual ELISA), chemiluminescence (e.g., automated CLIA, chemiluminescence resonance energy transfer (CRET)), florescence (e.g., manual immunoassays, ELISA, fluorescence resonance energy transfer (FRET)) and by the naked eye (e.g., lateral flow immunoassays).

The COVID-19 MIA can be used for the clinical detection of anti-SARS-CoV-2 antibodies in subjects using different immunoassay formats. For example, the COVID-19 MIA can be performed using a membrane (e.g., PictArray™, U.S. Pat. No. 9,625,453) or on the solid surface of 96-well microtiter plate (MTP). The antibodies (e.g., IgG) in the SARS-CoV-2 infected individuals can be detected via an indirect immunoassay, where multiple recombinant structural proteins of SARS-CoV-2, e.g., NP, SP and/or MP, will be coated on the membrane or the solid surface of MTP. The COVID-19 MIA can be automated using an analyzer that automates all the steps in the manual MIA and uses a colorimetric reader and image analysis software (e.g., PictImager™ and Pictorial ( ) The COVID-19 MIA can be performed as a lateral flow immunoassay (LFIA) or a manual singleplex ELISA assay.

Further, the COVID-19 MIA can be performed using chemiluminescent immunoassays (CLIAs), both multiplex as well as singleplex. The multiple structural proteins of SARS-CoV-2 can be bound covalently to paramagnetic beads (micron-sub-micron size) and used for the detection of IgG antibodies against SARS-CoV-2 via indirect immunoassay. The detection signal is generated by conjugating the detection antibody with acridinium or other chemiluminescent labels and generating a chemiluminescent signal.

The COVID-19 MIA can be performed by manual and automated wash-free assays for the detection of IgG.

The COIVD-19 MIA can also be performed as a wash-free electrochemiluminescent ELISA. The analytes in sample can be detected using biomolecule-coated (antigen-coated) carbon electrode surface-based microwell plates and SULFO-TAG-labelled detection Ab that emits light upon electrochemical stimulation.

Further, the COVID-19 MIA can be performed by centrifugal microfluidics-based automated immunoassay. The multiple structural proteins of SARS-CoV-2 can be covalently bound to paramagnetic beads and used for the detection of IgG antibodies generated in the subjects in response to SARS-CoV-2 infection. The detection of analyte occurs in a reaction chamber, followed by washing the specific immune complexes formed on paramagnetic beads and transfer of the paramagnetic beads to the detection chamber for the generation and reading of assay signal, which can be chemiluminescence, absorbance or fluorescence.

The COVID-19 MIA can also be performed as a lab-on-a-chip (LOC) assay. Paramagnetic beads or solid surfaces can be used for the covalent attachment of multiplex structural proteins of SARS-CoV-2. The detection signal could be chemiluminescent, fluorescent, absorbance, electrochemical or colorimetric Additionally, the COVID-19 MIA can be performed using manual singleplex ELISA. Paramagnetic beads can be bound covalently to multiplex structural proteins of SARS-CoV-2 to detect antibodies raised against SARS-CoV-2.

Further, the COVID-19 MIA can be a point of care (POC) immunoassay. The POC immunoassay can be label-free using a disposable strip, where the antibodies are detected using electrochemical reader or a smartphone-based reader.

In additional to the assay formats mentioned above, the COVID-19 MIA can be performed using wash-free immunoassay based on fluorescence resonance energy transfer (FRET) or chemiluminescence resonance energy transfer (CRET); signal-enhanced immunoassay based on the use of nanoparticle-based signal detection step or the use of micro- and submicro-beads for binding capture antibodies/antigens; and rapid multiplex immunoassays based on Lab-in-a-tube technology or vertical microfluidics.

The following examples are provided to further illustrate the embodiments of the present invention but are not intended to limit the scope of the invention. While they are typical of those that might be used, other procedures, methodologies, or techniques known to those skilled in the art may alternatively be used

EXAMPLES

Example 1

COVID-19 MIA

The COVID-19 MIA format involves the detection of IgG antibody (Ab) generated in humans after exposure to the SARS-CoV-2 virus.

The format will spot the SARS-CoV-2 structural proteins (e.g., Nucelocaspid protein (NP), spike protein (SP) and membrane protein (MP)) onto either membrane (e.g., nitrocellulose, nylon; such as PictArray™, U.S. Pat. No. 9,625,453) or membrane-free (e.g., polystyrene microtiter plate) assay surfaces. The capture antigens (Ag) and the detection Ab, used for the development of the COVID-19 MIA have already been identified, as shown in Table 1.

TABLE 1

Assay materials identified to be screened for use for the COVID-19 MIA
Table of assay materials used

| Vendor | Cat # | Product Name |
| --- | --- | --- |
| 1. Nucleocapsid Protein antigen | | |
| Bio Bench | nCoV-P003/XG01 | Nucleocapsid Protein, Fragment (N - protein) |

TABLE 1-continued

Assay materials identified to be screened for use for the COVID-19 MIA
Table of assay materials used

| Vendor | Cat # | Product Name |
|---|---|---|
| 2. Spike Protein antigen | | |
| The Native Antigen Company | REC31806 | SARS-CoV-2 Spike Glycoprotein (S1), Sheep Fc-Tag (HEK293) |
| 3. Anti-Human detection antibody | | |
| Immunobioscience | SA-9001-12 | Goat anti-Human IgG-HRP |

The generalized assay format for the COVID-19 MIA is summarised in FIG. 1. The IgG antibody against SARS-CoV-2 would be detected by indirect IA (FIG. 1A) (FIG. 1B). The SARS-CoV-2 structural proteins (NP, SP and MP) will be printed as spots onto the assay surface using a microarray printer in a single well. Additionally, NP, SP and MP can either be printed as separate discrete spots or a mixture of all three viral structural proteins printed as a single spot.

The COVID-19 kit will involve the printing of SARS-CoV-2 structural proteins on the assay surface (FIG. 2A) followed by the blocking of each well with an appropriate blocking solution to obviate any non-specific binding (FIG. 2B). The developed printed array will be supplied to the end-users along with the assay components for the detection Ab against SARS-CoV-2. Internal positive and negative controls will also be supplied which can be tested alongside patient samples to ensure optimal assay performance. Immunoassay (IA) procedures for the detection of Ab will involve the addition of diluted patient serum to the well(s) and incubating at 37° C. for tens of minutes so that specific immune complexes are formed between the Ag and Ab, e.g., binding of IgG to SARS-CoV-2 structural proteins (FIG. 2C). The excess and non-specifically bound analytes are then taken away by washing the wells with wash buffer. Subsequently, HRP-labelled detection Ab, e.g., anti-human IgG HRP and anti-NP HRP are added to the wells and incubated at 37° C. for tens of minutes (FIG. 2D). It results in the formation of biomolecular immune complexes between detection Ab and COVID-19 analytes. This is followed by second washing step with wash buffer that removes the excess and non-specifically bound analytes from the wells. Finally, HRP substrate is added to the wells and incubated for some minutes at room temperature. It leads to the formation of colorimetric array spots via the precipitation of the colorimetric product produced after the enzyme substrate reaction if the target analytes are present in the patient serum (FIG. 2E). This is followed by third washing step with wash buffer. In case of membrane-based IA, 3,3'-Diaminobenzidine (DAB) will be used as the HRP substrate and after incubation, the wells will be washed with wash buffer and then dried at 37° C. before analysis. But for membrane-free IA, a precipitating 3,3',5,5'-Tetramethylbenzidine (TMB) solution will be used as the HRP substrate and after incubation, the wells will be washed once prior to analysis.

The COVID-19 MIA results in the formation of colorimetric spots, the intensity of which is directly proportional to the concentration of IgG antibody present in the patient sample. Depending on the assay surface used, the colorimetric arrays are imaged by using indigenously developed handheld or portable benchtop colorimetric reader device. It can also be read by the commercial colorimetric readers, such as those available from Scienion AG, Germany.

Imaging software analyses the images from the multiplex colorimetric readers to detect the microarray spots from each well and generates the results as output. The software first identifies the wells and then detects the positive control spots within each well that appears after the MIA. The positive control spots act as alignment anchors, which are used by the software to place a microarray grid for all spots within each well. The software algorithm then analyses the colorimetric image of the array and extracts the pixel intensity for each spot. The data generated from each spot is then collated with the layout of array and patient samples to provide a final test report for the samples being analysed. An example of such imaging software is Pictorial©

Example 2

COVID-19 Mia-Membrane-Based, Single Well

The COVID-19 MIA-Membrane-based, Single well format utilises the 16-well array slide containing membrane disks affixed to the bottom of each well as the assay surface. SARS-CoV-2 structural proteins (NP, SP and MP) are all immobilised in duplicate as separate spots in each well.

The patient samples are diluted and added to the array slide and incubated at 37° C. then washed with wash buffer. HRP labelled anti-Human IgG detection Ab is then added to all wells of the array slide. The wells are incubated at 37° C. and then washed followed by the addition of DAB substrate. After a short incubation, the wells are washed once and then dried at 37° C. prior to analysis.

Example 3

COVID-19 Mia-Membrane-Based, Single Well, Using Grouped SARS-CoV-2 Structural Proteins The COVID-19 MIA-Membrane-based, Single well, using grouped SARS-CoV-2 structural proteins format utilises the 16-well array slide containing membrane disks affixed to the bottom of each well as the assay surface. A mixture of SARS-CoV-2 structural proteins (NP, SP and MP) are all immobilised in duplicate spots in each well.

The patient samples are diluted and added to the array slide, incubated at 37° C., and then washed with wash buffer. HRP labelled anti-Human IgG detection Ab is then added to all wells of the array slide. The wells are incubated at 37° C. and then washed followed by the addition of DAB substrate. After a short incubation, the wells are washed once and then dried at 37° C. prior to analysis.

Example 4

COVID-19 Mia-Membrane-Free, Single Well

The COVID-19 MIA (Membrane-free, Single well) format utilises the 96-well microtiter plate as the assay surface.

For each well in the 96-well plate, SARS-CoV-2 structural proteins (NP, SP and MP) are immobilised in duplicate as separate spots.

The patient samples are diluted and added to the 96-well plate, incubated at 37° C., and then washed with wash buffer. HRP labelled anti-Human IgG detection Ab is then added to all wells. The wells are incubated at 37° C. and then washed followed by the addition of TMB substrate. After a short incubation, the wells are washed once and then analysed.

Example 5

COVID-19 Mia-Membrane Free, Single Well, Using Grouped SARS-CoV-2 Structural Proteins The COVID-19 MIA (Membrane-free, Single well, using grouped SARS-CoV-2 structural proteins) format utilises the 96-well microtiter plate as the assay surface. For each well in the 96-well plate, a mixture of SARS-CoV-2 structural proteins (NP, SP and MP) are immobilised in duplicate.

The patient samples are diluted and added to the 96-well plate, incubated at 37° C., and then washed with wash buffer. A mixture of HRP labelled anti-NP detection Ab and HRP labelled anti-Human IgG detection Ab is added to all wells. The wells are incubated at 37° C. and then washed followed by the addition of TMB substrate. After a short incubation, the wells are washed once and then analysed.

Example 6

Automated COVID-19 MIA-Membrane Free, 96-Well MTP

The automated MIA will be performed inside an analyzer, where all the steps in the manual MIA will be automated. The dispensing and aspiration of reagents is done by a needle attached to the robotic arm. The assay components will be provided in the form of ready-to-use assay cartridges that are simply plugged inside the analyzer and can perform up to 100 MIA tests. The washing of the MTP wells will be done by the robotic needle using specific washing programs. Similarly, the needle will be washed after each dispensing step. However, disposable tips could also be used, which would obviate the cleaning of the needle after each dispensing step. All the steps of the IA will be optimized for the automated MIA. The readout of the colorimetric array spots in the processed 96-well MTP will be performed using an integrated colorimetric reader and an image analysis software. The analyzer would have a dedicated compartment for putting the patient sample vials, and dedicated spaces for putting the wash buffer, TMB substrate and other buffers. The analyzer would need to undergo daily, weekly and monthly maintenance.

Example 7

Automated Chemiluminescent Immunoassay (CLIA)

The assay formats used for development of MIA could be further employed for the development of automated CLIAs, both multiplex as well as singleplex, for the detection of anti-SARS-CoV-2 IgG antibodies. The multiple structural proteins of SARS-CoV-2 could be bound covalently to paramagnetic beads (micron-sub-micron size) and used for the detection of IgG antibodies against SARS-CoV-2 via indirect immunoassay. The magnetic beads could be provided with a mixture of multiple structural proteins or various formulations of magnetic beads could be coated with each of the structural proteins and then mixed together for the assays. The detection signal in case of automated CLIAs could be generated by conjugating the detection antibody with acridinium or other chemiluminescent labels and providing the appropriate trigger solutions for the generation of chemiluminescent signal. All the automated CLIAs are performed using a high-throughput analyzer. The assay reagents are stored in the form of assay cartridges that can used for up to 100 tests. The buffers, wash solution and trigger solutions are stored at the respective places in the analyzer. The patient sample vials are placed inside the analyzer at a dedicated place while the assay/reaction vials are provided automatically as consumable for each CLIA test.

Example 8

COVID-19 ELISA

Manual ELISA can be developed for the detection of IgG using the developed MIA procedure with customization of some steps for ELISA. The 96-well MTP would be coated with a mixture of NP, SP and/or MP either passively or using a leach-proof biomolecular immobilization procedure based on silane chemistry (Vashist et al., Sci Rep, 4:4407, 2014, DOI: 10.1038/srep04407). All the immunoassay steps for the detection of IgG ELISA would then be performed exactly as specified in the MIA except the last step. In case of ELISA, the signal would be generated by enzyme-substrate reaction by providing TMB and $H_2O_2$ to the HRP-labeled detection Ab. The enzyme-substrate reaction is stopped by providing a stop solution comprising of 1N $H_2SO_4$. The optical density of the colorimetric solution is then read at 450 nm with reference at 650 nm. The detection of IgG is done by indirect assay Materials. Reagents for the detection of IgG: SARS-CoV-2 NP, SARS-CoV-2 SP and, goat anti-human IgG-HRP. NP; and HRP labeled rabbit/mouse anti-SARS COV Ab (detection Ab).

Reagent set up: PBS: Add a BupH phosphate buffered saline pack to 100 ml of autoclaved DIW, dissolve well and make the volume up to 500 mL using autoclaved DIW. Each pack makes 500 mL of PBS at pH 7.2, which can be stored at room temperature (RT) for a week and at 4° C. for up to four weeks. APTES: The procured APTES solution has a purity of 99%. Reconstitute in autoclaved DIW to make 1% (v/v) APTES just before mixing with capture anti-HFA Ab.

Example 9

COVID-19 IgG/IgM ELISA

Mix COVID-19 structural antigens solution (mixture of NP, SP and/or MP) with 0.5-2% (v/v) APTES in the ratio of 1:1 (v/v). Incubate each of the desired wells of a 96-well MTP with 100 μL of the freshly prepared anti-NP capture Ab solution for 30 min at RT. Wash five times with 300 μL of 0.1M PBS, pH 7.4. Washing can also be performed with an automatic plate washer. (Passive Ab immobilization, by incubating with the Ab overnight at 4° C., could also done). Block the COVID-19 Ag-bound wells with 300 μL of 1-5% (w/v) BSA for 30 min at 37° C. followed by extensive PBS washing (as mentioned previously). Add 100 μL of varying human IgG concentrations or the patient serum/plasma sample (dilution to be determined after optimization) to different BSA-blocked wells. Incubate for 1 h at 37° C. and wash extensively with PBS (as stated previously). Add 100 μL of HRP-labeled anti-human IgG detection Ab (200 ng mL-1) in each of the NP-captured wells. Incubate for 1 h at 37° C. and wash extensively with PBS. Add 100 μL of TMB-$H_2O_2$ mixture to each of these wells and incubate at RT to develop color for 15 min. Stop the enzyme-substrate reaction by adding 50 µL of 1 N $H_2SO_4$ to each well. Determine the absorbance at a primary wavelength of 450 nm taking 540 nm as the reference wavelength in a microplate reader.

Example 10

Rapid One Step Kinetics-Based ELISA

A customized rapid one step kinetics-based rapid ELISA procedure could be employed for the detection of IgG, as specified in Vashist et al., Biosensors and Bioelectronics 67, 73-78, 2015.

Example 16

Rapid One Step Kinetics-Based ELISA Using Paramagnetic Beads

A customized rapid one step kinetics-based ELISA procedure could be developed using paramagnetic beads for the detection of IgG, as specified in Vashist et al., Analytical Biochemistry 456, 32-37, 2014.

Example 17

Centrifugal Microfluidics-Based Automated Point-of-Care Immunoassy

A customized centrifugal microfluidics-based automated point-of-care immunoassay procedure could be developed using paramagnetic beads for the detection of IgG, as conceived in Czilwik et al., RSC Advances 5 (76), 61906-61912, 2015.

Example 18

Wash-Free Immunoassay

Manual and automated wash-free MIAs could be developed for the detection of IgG. As an example, the IA for IgG would involve the specific biomolecular interactions of NP/SP/MP coated donor beads with another goat/rabbit/mouse anti-human Ab-coated acceptor beads in the presence of IgG in sample, which form immune complexes and generate a chemiluminescent signal as the donor and acceptor beads are in proximity. This format will substantially reduce the assay duration and complexity (no washing steps required) and would have high sensitivity and broad dynamic range.

Example 19

Summary of COVID-19 Multiplex Immunoassay (MIA)

The MIA format involves the simultaneous detection of IgG antibodies generated in humans after exposure to the SARS-CoV-2 virus. The format employs PictArray™ technology for the spotting of SARS-CoV-2 structural proteins (Nucleocapsid Protein (NP), spike protein (SP)) on membrane-free (i.e., polystyrene) assay surfaces.

The overall assay format for the COVID-19 MIA is summarised in FIG. 1. The IgG antibodies against SARS-CoV-2 are detected via indirect immunoassay. The SARS-CoV-2 structural proteins (NP and SP) are printed as spots on to the assay surface using a microarray printer, both proteins are printed within the same assay well. Additionally, NP and SP can either be printed as separate discrete spots or as a mixture of both proteins printed at a single spot.

After printing SARS-CoV-2 proteins on the assay surface (FIG. 2A), each well will be blocked with an appropriate blocking solution to eliminate any non-specific binding (FIG. 2B). The assay is divided into three distinct steps, with a duration of 1 hour and 5 minutes. In the first step of the assay, diluted patient serum is added, and the wells are incubated at 37° C. for 30 minutes to allow the binding of target analytes, i.e., IgG antibodies to SARS-CoV-2 proteins (FIG. 2C). The wells are washed with wash buffer to remove any unbound serum components, followed by step two, HRP-labelled detection antibodies, i.e., anti-Human IgG-HRP, are added, and the wells are incubated at 37° C. for 15 minutes to allow the detection of the target analytes (FIG. 2D). The wells are washed for a second time to remove any unbound detection antibodies. In the third step, HRP substrate is added (a precipitating 3,3',5,5'-Tetramethylbenzidine (TMB) solution), and the wells are incubated at room temperature (21° C.-25° C.) for 20 minutes to allow the visualisation of the array spots that the target analytes present in the serum bind to (FIG. 2E).

Example 20

COVID-19 MIA-Membrane Based, SARS CoV-2, Structural Proteins Printed in Dublicate The printed spots in the COVID-19 MIA are shown as shaded circles where each circle of a particular shade corresponds to a specific SARS-CoV-2 structural protein that is printed on the membrane or the solid surface (FIG. 7A-B). The white circles signify that nothing has been printed at that specific position.

The plate preparation and spotting were performed as follows. Each antigen (SARS-CoV-2 NP and SARS-CoV-2 SP (S1)) was diluted in NP-40 0.05% (1 volume of NP-40 0.05% in 9 volumes of antigen) and incubated for 15 min at room temperature (20° C. to 25° C.), followed by the addition of 2× print buffer (2× PB) and RO water. The final solution has the antigen concentrations at 200 µg/ml and 200 µg/ml in 1× print buffer (1× PB) for SARS-CoV-2 NP and SARS-CoV-2 SP, respectively. Biotinylated goat anti-mouse IgG is used as a positive control to confirm the addition of the secondary antibody solution and aids in the alignment of the image analysis software during the analysis of results. Biotinylated goat anti-mouse IgG is printed at a concentration of 20 µg/ml, in PB and RO water. Print buffer is printed as the negative control in the assay. It indicates the overall assay background. Twenty eight µL of each of the prepared proteins and print buffer solution were transferred in a 384-well PCR plate for printing. The printing was performed using the Thomas™ microarrayer under the following conditions: temperature 23° C. and relative humidity 56%. The pin is washed in RO water before each spot is printed. Visual quality control of the printed array was performed to check spot positioning and morphology. The slides were then dried for 30 minutes at 37° C. . . . Seventy five µL of blocking solution was added to each slide well and incubated at 37° C. for 30 minutes. Slides were inverted and tapped to remove the blocking solution and dried for 15 minutes at 37° C. . . . The dried slides were stored at 2-8° C. in a plastic box with desiccants.

Slides were brought to room temperature prior to be used. One volume of serum/plasma sample was added to 9 volumes of assay diluent (1:10 dilution). Fifty µL of diluted sample was dispensed in each well and then, the slides were covered (using a plate cover) and incubated for 1 hour at 37° C., followed by washing 3 times using 60 µL of washing solution per well for each wash. Any excess liquid was removed by inverting the slides. Fifty µL of the secondary antibody (0.5 µg/ml) was added to each slide well, which was then cover and incubated for 30 minutes at 37° C. . . .

The slide was washed using 60 μL of washing solution per well for three wash steps. Any excess liquid was removed by inverting the slide. Fifty μL of DAB substrate diluted in hydrogen peroxide ($H_2O_2$) (1 volume of DAB in 19 volumes of $H_2O_2$) was added to each well of the slide and incubated for 5 minutes at room temperature in the dark. DAB was then removed by inverting and tapping the slide onto an absorbent tissue. The slides were washed once using the washing solution, inverted and then dried 15 minutes at 37° C. . . . The slides were read using the PictImager™ reader and the data automatically processed once the slides were scanned by the Pictorial© software.

The COVID-19 MIA was assessed against the first WHO international reference panel for anti-SARS-CoV-2 immunoglobulin, which is made up of five referenced samples that have different reactivities against NP and SP printed on our platform. Using SARS-CoV-2 NP as the target, the assay signals for the reference panel correlated to the reactivity levels indicated by the provider, i.e., the signal decreased from the highly reactive sample to the low reactive one, and no reactivity for the negative sample (FIG. 8).

Example 21

COVID-19 MIA-Membrane Free, Single Well

The printed spots in the COVID-19 MIA are shown as shaded circles where each circle of a particular shade corresponds to a specific SARS-CoV-2 structural protein that is printed on the membrane or the solid surface (FIG. 9A-B). The white circles signify that nothing has been printed at that specific position.

The plate preparation and spotting were performed as follows. Each antigen (SARS-CoV-2 NP and SARS-CoV-2 SP (S1)) was diluted in NP-40 0.05% (1 volume of NP-40 0.05% in 9 volumes of antigen) and incubated for 15 min at room temperature, followed by the addition of 2× PB and RO water. The final solution has the antigen concentrations at 100 μg/ml and 200 μg/ml in 1× PB for SARS-CoV-2 NP and SARS-CoV-2 SP, respectively. Biotinylated goat anti-mouse IgG, used as a positive control to confirm the addition of the secondary antibody solution, also aids in the alignment of the image analysis software during the final analysis of results. Biotinylated goat anti-mouse IgG is printed as the positive control at a concentration of 20 μg/ml, in PB and RO water. Print buffer is printed as the negative control in the assay. It indicates the overall assay background. Twenty eight μL of each of the prepared proteins and print buffer solution were transferred in a 384-well PCR plate for printing. The printing was performed using the Thomas™ microarrayer under the following conditions temperature 21.6° C. and relative humidity 40-43%. The pin is washed in RO water before each spot is printed. Visual quality control of the printed array was performed to check spot positioning and morphology, before being sealed (parafilm) and incubated for ~22 h at 2-8° C. . . . Two hundred μL of blocking solution was added to each well of the microtiter plate, which was then incubated at room temperature for 1 h. Plates were then washed three times with 300 μL of washing solution. Any remaining liquid was removed, and plates were left to dry for 20 min at room temperature. The dried plates were sealed and stored at 2-8° C. . . .

Plates were brought to room temperature prior to being used. One volume of serum/plasma sample was added to 100 volumes of assay diluent (1:101 dilution). Dilution ratios for anti-NP reconstructed human mAb, IgG and anti-Spike-RBD human reconstructed mAb, IgG were adjusted to make a final concentration of 1 μg/ml for each Ab. The samples were prepared in 1.1 ml tubes by mixing the added samples with the assay diluent via multiple aspiration and dispensing runs. This was followed by the dispensing of 100 μL of each sample into the specific wells on the microtiter plate. The plate was then sealed (parafilm) and incubated for 30 minutes at 37° C., followed by washing the plate 3 times using 300 μL of washing solution per well for each wash. Any excess liquid was removed by tapping the plate. One hundred μL of the secondary antibody (0.2 μg/ml) was added to each well of microtiter plate, which was then sealed (parafilm) and incubated for 15 minutes at 37° C., followed by plate washing using 300 μL of washing solution per well for three wash steps. Any excess liquid was removed by inverting and tapping the plate. One hundred μL of Pierce 1-step ultra TMB Blotting solution was added to each well of the microtiter plate, which was then incubated for 20 minutes at room temperature in the dark. The TMB was then removed by inverting and tapping the plate onto an absorbent tissue, removing any remaining liquid. Plate was read within 5 min. The plate was read using the sciREADER CL2, and the "R&D Imaging & Analysis" software. The camera focus was set to 270 during the reading. The assay background was calculated based on four chosen positions across a well.

The results showed that the method used to clean the pin was effective. The efficiency of the cleaning method is shown FIG. 10, where there are no appearance of colored spots at places where the print buffer was printed.

The casein-based blocker used was very efficient in preventing non-specific binding within wells while maintaining the spots' morphology. This is demonstrated in FIG. 11D-E, where a plasma sample reactive to both printed targets was compared to a non-reactive sample. For both samples, there is no excessive background in the well for the reactive sample, as the assay spots are clearly differentiable from the background.

The signals obtained during the analysis of results, are automatically processed by the software, which calculates the mean of each spot intensity and subtracts the background (FIG. 10). The presence of airborne particles at the bottom of the well occasionally increases the background signal. In these cases, an absolute value of 72 AU was used as the background median value. As each protein is printed in duplicate per well, the median of two replicates signals was used as the well's intensity. For the results presented, each sample was run in two wells, results are therefore an average of four reactive spots (duplicate spots from two wells).

The ability of the assay to differentiate between anti-SARS-CoV-2 NP IgG antibodies and anti-SARS-CoV-2 SP S1 IgG antibodies was tested using the Anti-NP reconstructed human mAb, IgG (anti-NP mAb) and Anti-Spike-RBD human reconstructed mAb, IgG (Anti-Spike-RBD). When the anti-NP mAb was used as the sample, only the assay spots printed with SARS-CoV-2 NP resulted in a positive reaction (FIG. 11B). On the contrary, when the anti-Spike-RBD mAb was used as the sample, only the assay spots with anti-SARS-CoV-2 SP reacted positively (FIG. 11C).

Two control samples were used to evaluate the performance of the COVID-19 MIA. One of them was the anti-SARS-CoV-2 antibody, a sample collected from a COVID-19 PCR positive-confirmed patient at least 4 weeks after symptoms and recovery. This control showed good reactivity and a CV of less than 10% on both SARS-CoV-2 NP and SARS-CoV-2 SP S1 targets (Table 1). The second control material was anti-SARS-CoV-2 QC1, a sample obtained from two convalescent plasma packs known to be SARS-CoV-2 positive. This sample has shown a strong reactivity for SARS-CoV-2 NP but a low reactivity for SARS-CoV-2 SP. The results had CV of less than 5% for both NP and SP targets (Table 1).

TABLE 1

Assessment of some positive controls and the First WHO International Standard for Anti-SARS-CoV-2 IgG (human).

| Samples tested | SARS-CoV-2 Nucleocapsid Protein as target | | SARS-CoV-2 Spike Protein (S1) as target | |
|---|---|---|---|---|
| | Means | CV | Means | CV |
| Anti-SARS-CoV-2 Antibody | 70.9 | 8% | 31.3 | 8% |
| Anti-SARS-CoV-2 QC1 | 58.2 | 1% | 10.7 | 0% |
| First WHO International Standard for Anti-SARS-CoV-2 IgG | 68.7 | 7% | 53.9 | 16% |

The assay was evaluated using the first WHO international standard for anti-SARS-CoV-2 immunoglobulin (human). The reactivities obtained for both targets were high, however, the CV for the SARS-CoV-2 SP S1 was approximately 16% (Table 1). Even though the results were promising, the assay was assessed using another reference panel. The first WHO international reference panel for anti-SARS-CoV-2 immunoglobulin, is made up of five referenced samples, which have different reactivities against NP and SP. Using SARS-CoV-2 SP S1 as the target, the assay signals for the reference panel correlated to the reactivity levels indicated by the provider, i.e., the signal decreased from the highly reactive sample to the low reactive one, and there was no signal for the negative sample (FIG. 12).

The performance of developed assay was compared with that of other commercial tests using the samples in the NIBSC anti-SARS-CoV-2 verification panel. The panel comprises 37 samples, 23 samples from convalescent plasma packs known to be anti-SARS-CoV-2 positive and 14 from convalescent plasma packs known to be anti-SARS-CoV-2 negative. All samples were tested using several commercial tests. The results obtained are summarized in Table 2. As the developed assay can detect the IgG antibodies against SARS-CoV-2 NP and IgG antibodies against SARS-CoV-2 SP S1 in a single well, the results obtained with each target were compared to the commercial tests that use the same target in their assay for NP and SP, i.e., SARS-CoV-2 NP and SARS-CoV-2 SP (S1). Except for the Pictor assay, the values reported in the table are taken from the datasheet of NIBSC panel. The values for the Pictor assay are the average of two replicates. Please note that the values are different for each company, which cannot be compared as they employ different readout mechanisms.

For both viral proteins, the 23 positive samples generate very strong signals, which can clearly be differentiated from the negligible signals obtained using the 14 negative samples. The results obtained correlate with the results obtained by other commercial tests. For the SARS-CoV-2 NP spots, the negative samples have a signal below 3 AU (Arbitrary Units). The only exception is panel #34, which has a signal of 5.8 that is still very low considering the lowest signal obtained across the positive ones is 52.3 AU for panel #16. Whereas for SARS-CoV-2 SP (S1) spots, there was no reactivity obtained on any of the negative samples tested.

TABLE 2

Assessment of the Anti-SARS-CoV-2 NIBSC verification panel for serology assays.

| Panel # | SARS-CoV-2 Nucleocapsid Protein as target | | | | SARS-CoV-2 Spike Glycoprotein (S1) as target | | | |
|---|---|---|---|---|---|---|---|---|
| | Abbott Architect | Euro-Immun | ROCHE Elecsys | Pictor | Liaison (S1/S2) | Siemens (S1, RBD) | Euro-Immun | Pictor |
| 1 | 3.7 | 2.7 | 17.2 | 85.9 | 20.2 | 0.6 | 1.7 | 34.9 |
| 2 | 1.4 | 2.1 | 8.8 | 65.6 | 37.5 | 0.98 | 3.2 | 46.2 |
| 3 | 6.5 | 6.2 | 50.7 | 85.3 | 260.7 | >20.0 | 8.5 | 89.3 |
| 4 | 4.2 | 3.7 | 27.5 | 86.2 | 202 | >20.0 | 7.9 | 88.2 |
| 5 | 7.2 | 5.8 | 90.5 | 67.0 | 226 | >20.0 | 8.5 | 76.1 |
| 6 | 4.2 | 3.1 | 54.9 | 53.9 | 75 | 12.2 | 5.8 | 47.3 |
| 7 | 4 | 2.9 | 8.9 | 58.4 | 105.3 | 8.8 | 5.7 | 59.1 |
| 8 | 7.2 | 5 | 101.3 | 67.2 | 163 | >20.0 | 7.1 | 72.2 |
| 9 | 5.8 | 5.6 | 50.1 | 88.5 | 166.7 | >20.0 | 7.9 | 90.0 |
| 10 | 5.8 | 5.5 | 49.9 | 84.6 | 174.3 | >20.0 | 8 | 84.4 |
| 11 | 1.8 | 1.4 | 14.2 | 59.1 | 74.7 | 4.2 | 4.6 | 61.6 |
| 12 | 4.4 | 3.4 | 51 | 81.1 | 86.2 | 4.7 | 4.9 | 62.9 |
| 13 | 6.4 | 4.3 | 101.7 | 58.9 | 87.4 | 5.4 | 5.1 | 38.6 |
| 14 | 4.5 | 3.3 | 70.1 | 53.9 | 88.5 | 5.3 | 4.8 | 36.1 |
| 15 | 5.3 | 3.9 | 108 | 68.2 | 110.7 | 6.5 | 5.7 | 51.9 |
| 16 | 1.2 | 2.4 | 4.6 | 52.3 | 79.1 | 1.9 | 4.2 | 34.8 |
| 17 | 3.9 | 3.1 | 26.6 | 91.7 | 111.7 | 12.2 | 6.1 | 73.9 |
| 18 | 6.4 | 4.9 | 82.5 | 87.6 | 161.3 | >20.0 | 7.6 | 83.6 |
| 19 | 5.1 | 5.1 | 58.8 | 86.2 | 148 | 12.2 | 5.8 | 62.4 |
| 20 | 4.5 | 3.3 | 141.7 | 78.3 | 145.7 | 10.3 | 6.2 | 76.5 |
| 21 | 7 | 4.9 | 108.3 | 71.7 | 117.3 | 15.2 | 6.6 | 28.4 |
| 22 | 5.5 | 3.5 | 132 | 64.3 | 151 | 13.5 | 6.7 | 54.7 |
| 23 | 5 | 3.4 | 123.3 | 65.1 | 140.7 | 8.4 | 6.5 | 57.8 |

TABLE 2-continued

Assessment of the Anti-SARS-CoV-2 NIBSC verification panel for serology assays.

| | SARS-CoV-2 Nucleocapsid Protein as target | | | | SARS-CoV-2 Spike Glycoprotein (S1) as target | | | |
|---|---|---|---|---|---|---|---|---|
| Panel # | Abbott Architect | Euro-Immun | ROCHE Elecsys | Pictor | Liaison (S1/S2) | Siemens (S1, RBD) | Euro-Immun | Pictor |
| 24 | 0.02 | 0.05 | 0.02 | 0.0 | <3.8 | 0 | 0.09 | 0.0 |
| 25 | 0.05 | 0.1 | 0.08 | 1.3 | <3.8 | 0.03 | 0.08 | 0.4 |
| 26 | 0.12 | 0.17 | 0.07 | 2.9 | <3.8 | 0.01 | 0.39 | 0.0 |
| 27 | 0.01 | 0.03 | 0.07 | 0.3 | <3.8 | 0 | 0.08 | 0.0 |
| 28 | 0.05 | 0.03 | 0.07 | 0.0 | <3.8 | 0 | 0.07 | 0.0 |
| 29 | 0.01 | 0.02 | 0.07 | 0.0 | <3.8 | 0 | 0.06 | 0.0 |
| 30 | 0.16 | 0.15 | 0.08 | 0.0 | <3.8 | 0.01 | 0.27 | 0.0 |
| 31 | 0.01 | 0.09 | 0.07 | 0.0 | <3.8 | 0 | 0.1 | 0.0 |
| 32 | 0.03 | 0.04 | 0.07 | 0.0 | <3.8 | 0 | 0.11 | 0.0 |
| 33 | 0.04 | 0.08 | 0.07 | 1.2 | <3.8 | 0 | 0.11 | 0.3 |
| 34 | 0.01 | 0.18 | 0.08 | 5.8 | <3.8 | 0 | 0.09 | 0.0 |
| 35 | 0.01 | 0.05 | 0.07 | 0.8 | 8.43 | 0 | 0.07 | 0.0 |
| 36 | 0.04 | 0.2 | 0.07 | 0.0 | <3.8 | 0 | 0.07 | 0.0 |
| 37 | 0.03 | 0.06 | 0.07 | 0.0 | <3.8 | 0 | 0.12 | 0.0 |

Example 22

COVID-19 MIA-Membrane Free, Single Well, with Grouped SARS-CoV-2 Structural Proteins The printed spots in the COVID-19 MIA are shown as shaded circles, where each circle of a particular shade corresponds to a specific SARS-CoV-2 structural protein that is printed on the membrane or the solid surface (FIG. 13A-B). The white circles signify that nothing has been printed at that specific position.

The plate preparation and spotting were performed as follows. One volume of NP-40 0.05% was added to 9 volumes of antigens solution made up of SARS-CoV-2 NP & SARS-CoV-2 SP (S1). The preparation was incubated for 15 min at room temperature. This is followed by the addition of 2× PB and the required volume of RO water to the solution so that the target antigen and print buffer concentrations are achieved. The final solution contained SARS-CoV-2 NP at 100 µg/ml and SARS-CoV-2 SP (S1) at 200 µg/ml in 1× PB. Biotinylated goat anti-mouse IgG is used as positive control. It is used to ascertain that the secondary antibody solution was added to the well and helps the image analysis software to detect the printed array. It was printed at a concentration of 20 µg/ml, which was achieved via a dilution in 2× PB and RO water. The print buffer is printed as such on the array and is used as negative control for the assay. It indicates the quality of printing, the intensity of background induced by the print buffer alone, and the overall assay background. Twenty eight µL of each of the prepared proteins and print buffer solution were transferred in a 384-well PCR plate for printing. The printing was performed using the Thomas™ microarrayer. The temperature inside the arrayer during the printing was 22.8° C., while the humidity was between 40%. The array was printed in three steps: 1) spots A1, C1, E1 were printed first, which is followed sequentially by the printing of spots A2 & A3, and E2, E3 & E5. Before each spot is printed, the arrayer washes the pin with RO water in the washing chamber and dries it in the drying chamber. The consecutive wash and dry steps are performed three times and then the pin goes in the next source plate's well to collect the preparation and starts the printing of respective spots. A visual quality control of the printed array was done to ensure that the spots were at the right position and had a good morphology. The plates were then sealed with parafilm and incubated for ~19 h at 2-8° C. in a refrigerator. The blocker was stored between 2 to 8° C. (with an average temperature of 4° C.) since the preparation day. It was left at room temperature for 25 min prior to being used, while the plate was left at the same temperature for 5 min prior to being blocked. Two hundred µL of blocking solution was added to each well of the microtiter plate, which was then sealed using parafilm and incubated at room temperature for 1 h. This was followed by washing the plate three times on a plate washer with 300 µL of washing solution. The washed plate was then tapped onto an absorbent tissue to remove any remaining liquid and left in the biosafety cabinet for 20 min at room temperature. The dried plate was sealed and stored at 2-8° C. in a refrigerator.

The plate was left at room temperature for 30 min prior to being used. One volume of sample was added to 100 volumes of assay diluent (1:100 dilution). However, appropriate dilution ratios were used for anti-NP reconstructed human mAb, IgG and anti-Spike-RBD human reconstructed mAb, IgG to make a final concentration of 1 µg/ml for each Ab. The samples were prepared in 1.1 ml tubes by mixing the added samples with the assay diluent via multiple aspiration and dispensing runs. This was followed by the dispensing of 100 µL of each sample into the specific wells on the microtiter plate. The plate was then sealed using a parafilm and incubated for 30 minutes at 37° C. This was followed by washing the plate 3 times using 300 µL of washing solution per well for each wash. The washed plate was then tapped onto an absorbent tissue to remove any remaining liquid. One hundred µL of the secondary antibody (0.2 µg/ml) was added to each well of the microtiter plate, which was then sealed using a parafilm and incubated for 15 minutes at 37° C. This was followed by washing the plate 3 times using 300 µL of washing solution per well for each wash. The washed plate was then tapped onto an absorbent tissue to remove any remaining liquid. One hundred µL of Pierce 1-step ultra TMB Blotting solution was added to each well of the microtiter plate, which was then covered and incubated for 20 minutes at room temperature in the dark. The TMB was then removed by inverting the plate, which was tapped onto an absorbent tissue to remove any remaining liquid and read within 5 min. The plate was read using the sciREADER CL2, and the "R&D Imaging & Analysis" section of the software was used to read the plate. The camera focus was 270 during the reading. The assay background was calculated based on four chosen positions across a well.

The results showed that the method used to clean the pin was effective. The efficiency of the cleaning method is shown FIG. 14, where no colored spots appeared at places where the print buffer was printed.

The casein-based blocker used was very efficient in protecting the non-specific binding in wells while maintaining the spots' morphology. It is demonstrated in FIG. 15D-E where a plasma sample reactive to both printed targets and a non-reactive one was tested. For both samples, there is no excessive background in the well and for the reactive sample, the assay spots are clearly differentiable from the background.

The signal used during the analysis are automatically processed by the software, which calculates the mean of each spot intensity and subtracts the background (FIG. 14). The presence of some airborne particles at the bottom of the well may increase the background signal. For those cases, an absolute value of 72 AU was used as the background median value. As each protein is printed in duplicate per well, the median of the two replicates signal was used as the well's intensity. Each sample was run in two wells. Therefore, the values reported here are the summary of those duplicates.

To demonstrate the capability of the platform to give a signal if the sample is only positive for anti-SARS-CoV-2 NP IgG antibodies or anti-SARS-CoV-2 SP S1 IgG antibodies, it was tested against the following monoclonal antibodies: anti-NP reconstructed human mAb, IgG (anti-NP mAb) and anti-Spike-RBD human reconstructed mAb, IgG (Anti-Spike-RBD). The assay spots were visible both when anti-NP mAb (FIG. 15B) and anti-Spike-RBD mAb were used as samples (FIG. 15C).

Two control samples were used. The anti-SARS-CoV-2 antibody gave good results with a CV of less than 10% (Table 3). Similarly, anti-SARS-CoV-2 QC1 also showed good results with a CV of around 12% (Table 3).

TABLE 3

Assessment of some positive controls and the First WHO International Standard for Anti-SARS-CoV-2 IgG (human)

| Samples tested | SARS-CoV-2 Nucleocapsid Protein & Spike (S1) as target | |
|---|---|---|
| | Means | CV |
| Anti-SARS-CoV-2 Antibody | 66.6 | 8% |
| Anti-SARS-CoV-2 QC1 | 29.3 | 12% |
| First WHO International Standard for Anti-SARS-CoV-2 IgG | 71.9 | 12% |

The developed assay was evaluated using the first WHO international standard for anti-SARS-CoV-2 immunoglobulin (human), which showed good results with a CV of about 12% (Table 3). Further, the first WHO international reference panel for anti-SARS-CoV-2 immunoglobulin was also tested. The assay signals correlated to the levels indicated by the provider, i.e., the signals decrease from the high reactive panel sample to the low reactive one and there was no signal for the negative sample. However, it is important to take into consideration the standard deviation of samples (FIG. 16).

The performance of the developed assay was compared with that of other commercial tests using the samples in the anti-SARS-CoV-2 verification panel. The panel comprises 37 samples, which has twenty-three samples from convalescent plasma packs known to be anti-SARS-CoV-2 positive and fourteen from convalescent plasma packs known to be anti-SARS-CoV-2 negative. All samples were tested using several commercial tests. The results obtained are summarized in Table 4. As the developed assay can detect the IgG antibodies against SARS-CoV-2 NP and IgG antibodies against SARS-CoV-2 SP S1 in a single well, the results obtained with each target were compared to the commercial tests that use the same target in their assay for NP and SP, i.e., SARS-CoV-2 NP and SARS-CoV-2 SP (S1).

For both viral proteins, the twenty-three positive samples generate very strong signals, which can clearly be differentiated from the negligible signals obtained using the fourteen negative samples. The results obtained correlate with the results obtained by other commercial tests. The negative samples had signals of less than 1 AU.

Except for Pictor, the values reported in the table are taken from the datasheet of NIBSC panel. The values for Pictor are the average of two replicates. Please note that the values are different for each company, which cannot be compared as they employ different readout mechanisms.

TABLE 4

Assessment of the Anti-SARS-CoV-2 verification panel for serology assays.

| Panel # | SARS-CoV-2 Nucleocapsid Protein as target | | | SARS-CoV-2 Spike Glycoprotein (S1) as target | | | |
|---|---|---|---|---|---|---|---|
| | Abbott Architect | Euro-Immun | ROCHE Elecsys | Euro-Immun | Liaison (S1/S2) | Siemens (S1, RBD) | Pictor |
| 1 | 3.7 | 2.7 | 17.2 | 1.7 | 20.2 | 0.6 | 87.6 |
| 2 | 1.4 | 2.1 | 8.8 | 3.2 | 37.5 | 1.0 | 70.8 |
| 3 | 6.5 | 6.2 | 50.7 | 8.5 | 260.7 | >20.0 | 86.5 |
| 4 | 4.2 | 3.7 | 27.5 | 7.9 | 202.0 | >20.0 | 87.2 |
| 5 | 7.2 | 5.8 | 90.5 | 8.5 | 226.0 | >20.0 | 72.4 |
| 6 | 4.2 | 3.1 | 54.9 | 5.8 | 75.0 | 12.2 | 58.0 |
| 7 | 4.0 | 2.9 | 8.9 | 5.7 | 105.3 | 8.8 | 67.3 |

TABLE 4-continued

Assessment of the Anti-SARS-CoV-2 verification panel for serology assays.

| Panel # | SARS-CoV-2 Nucleocapsid Protein as target | | | SARS-CoV-2 Spike Glycoprotein (S1) as target | | | |
|---|---|---|---|---|---|---|---|
| | Abbott Architect | Euro-Immun | ROCHE Elecsys | Euro-Immun | Liaison (S1/S2) | Siemens (S1, RBD) | Pictor |
| 8 | 7.2 | 5.0 | 101.3 | 7.1 | 163.0 | >20.0 | 76.1 |
| 9 | 5.8 | 5.6 | 50.1 | 7.9 | 166.7 | >20.0 | 96.9 |
| 10 | 5.8 | 5.5 | 49.9 | 8 | 174.3 | >20.0 | 91.6 |
| 11 | 1.8 | 1.4 | 14.2 | 4.6 | 74.7 | 4.2 | 68.4 |
| 12 | 4.4 | 3.4 | 51.0 | 4.9 | 86.2 | 4.7 | 76.7 |
| 13 | 6.4 | 4.3 | 101.7 | 5.1 | 87.4 | 5.4 | 66.7 |
| 14 | 4.5 | 3.3 | 70.1 | 4.8 | 88.5 | 5.3 | 60.9 |
| 15 | 5.3 | 3.9 | 108.0 | 5.7 | 110.7 | 6.5 | 77.9 |
| 16 | 1.2 | 2.4 | 4.6 | 4.2 | 79.1 | 1.9 | 61.6 |

TABLE 4-continued

Assessment of the Anti-SARS-CoV-2 verification panel for serology assays.

| Pan-el # | SARS-CoV-2 Nucleocapsid Protein as target | | | SARS-CoV-2 Spike Glycoprotein (S1) as target | | | |
|---|---|---|---|---|---|---|---|
| | Abbott Architect | Euro-Immun | ROCHE Elecsys | Euro-Immun | Liaison (S1/S2) | Siemens (S1, RBD) | Pic-tor |
| 17 | 3.9 | 3.1 | 26.6 | 6.1 | 111.7 | 12.2 | 94.1 |
| 18 | 6.4 | 4.9 | 82.5 | 7.6 | 161.3 | >20.0 | 89.8 |
| 19 | 5.1 | 5.1 | 58.8 | 5.8 | 148.0 | 12.2 | 78.8 |
| 20 | 4.5 | 3.3 | 141.7 | 6.2 | 145.7 | 10.3 | 71.9 |
| 21 | 7.0 | 4.9 | 108.3 | 6.6 | 117.3 | 15.2 | 71.9 |
| 22 | 5.5 | 3.5 | 132.0 | 6.7 | 151.0 | 13.5 | 66.4 |
| 23 | 5.0 | 3.4 | 123.3 | 6.5 | 140.7 | 8.4 | 71.2 |
| 24 | 0.0 | 0.1 | 0.0 | 0.09 | <3.8 | 0.0 | 0.0 |
| 25 | 0.1 | 0.1 | 0.1 | 0.08 | <3.8 | 0.0 | 0.0 |
| 26 | 0.1 | 0.2 | 0.1 | 0.39 | <3.8 | 0.0 | 0.0 |
| 27 | 0.0 | 0.0 | 0.1 | 0.08 | <3.8 | 0.0 | 0.0 |
| 28 | 0.1 | 0.0 | 0.1 | 0.07 | <3.8 | 0.0 | 0.0 |
| 29 | 0.0 | 0.0 | 0.1 | 0.06 | <3.8 | 0.0 | 0.0 |
| 30 | 0.2 | 0.2 | 0.1 | 0.27 | <3.8 | 0.0 | 0.0 |
| 31 | 0.0 | 0.1 | 0.1 | 0.1 | <3.8 | 0.0 | 0.0 |
| 32 | 0.0 | 0.0 | 0.1 | 0.11 | <3.8 | 0.0 | 0.0 |
| 33 | 0.0 | 0.1 | 0.1 | 0.11 | <3.8 | 0.0 | 0.0 |
| 34 | 0.0 | 0.2 | 0.1 | 0.09 | <3.8 | 0.0 | 0.0 |
| 35 | 0.0 | 0.1 | 0.1 | 0.07 | 8.4 | 0.0 | 0.0 |
| 36 | 0.0 | 0.2 | 0.1 | 0.07 | <3.8 | 0.0 | 0.0 |
| 37 | 0.0 | 0.1 | 0.1 | 0.12 | <3.8 | 0.0 | 0.0 |

Although the invention has been described with reference to the above examples, it will be understood that modifications and variations are encompassed within the spirit and scope of the invention. Accordingly, the invention is limited only by the following claims.

What is claimed is:

1. A substrate for surface plasmon resonance, localized surface plasmon resonance or interferometry detection comprising:
at least two capture elements specific for SARS-CoV-2 on the substrate, each capture element corresponding to and being able to bind a target analyte, and optionally a plurality of control elements selected from:
 a) at least one fiduciary marker,
 b) at least one negative control to monitor background signal,
 c) at least one negative control to monitor assay specificity,
 d) at least one positive colorimetric control, and/or
 e) at least one positive control to monitor assay performance and any combination thereof,
wherein the capture elements are a SARS-CoV-2 structural protein, and
wherein the target analyte is an anti-SARS-CoV-2 antibody.

2. The substrate of claim 1, wherein the capture elements bind target analytes, wherein the target analytes are antibodies produced in response to SARS-CoV-2 infection.

3. The substrate of claim 1, wherein the capture elements are selected from a SARS-CoV-2 Membrane protein (MP), Nucleocapsid protein (NP), Spike protein (SP), or any combination thereof.

4. The substrate of claim 1, wherein the substrate is a solid or porous substrate.

5. The substrate of claim 4, wherein the solid substrate is a paramagnetic bead, microtiter plate, microparticle, or a magnetic bead.

6. The substrate of claim 4, wherein the porous substrate is a membrane.

7. A kit for detecting a plurality of target analytes in a sample, comprising
 a) a substrate of claim 1 and optionally one or both of
 b) a background reducing reagent, and
 c) a colorimetric detection system.

8. The kit of claim 7, further comprising one or more items selected from the group consisting of: a) a wash solution, b) one or more antibodies for detection of antigens, ligands or antibodies bound to the capture elements or for detection of the positive controls, c) software for analyzing captured target analytes, and d) a protocol for measuring the presence of target analytes in samples.

9. The kit of claim 8, wherein the antibodies for detection comprise antibody-binding protein (BP) conjugates, antibody-enzyme label conjugates, or any combination thereof.

10. The kit of claim 8, wherein the sample is a blood or saliva sample.

11. The kit of claim 10, wherein the blood sample is serum or plasma.

12. The kit of claim 7, wherein the substrate is a solid or porous substrate.

13. The kit of claim 12, wherein the solid substrate is a paramagnetic bead, microtiter plate, or microparticle.

14. The kit of claim 12, wherein the porous substrate is a membrane.

15. A method of detecting anti-SARS-CoV-2 antibodies produced in a subject comprising:
 contacting a substrate of claim 1 with a biological sample from the subject, wherein the subject is suspected of having COVID-19 or is exposed to SARS-CoV-2; and
 detecting the presence of an antibody produced in response to SARS-CoV-2 infection.

16. The method of claim 15, wherein the antibody is IgG.

17. The method of claim 15, wherein the sample is a blood or saliva sample.

18. A method for processing a microarray comprising:
 a) providing a substrate of claim 1;
 b) adding at least one sample to the substrate; and
 c) processing the substrate such that a detectable result is given by two or more of i) at least one fiduciary marker, ii) at least one positive colorimetric control, and iii) at least one positive control to monitor assay performance.

19. The method of claim 18, wherein the blood sample is serum or plasma.

20. A method for detecting an analyte in a sample comprising providing a substrate of claim 1,
 adding at least one sample to the substrate, and
 processing the substrate such that a detectable result is provided.

21. The method of claim 20, wherein the detectable result includes two or more of at least one fiduciary marker, at least one positive colorimetric control, and at least one positive control to detect an analyte in the sample.

* * * * *